United States Patent
Bonutti et al.

[11] Patent Number: 5,453,075
[45] Date of Patent: Sep. 26, 1995

[54] ORTHOSIS WITH DISTRACTION THROUGH RANGE OF MOTION

[75] Inventors: Peter M. Bonutti, 1303 W. Evergreen Plaza, Effingham, Ill. 62401; Gary E. Zitzmann, Newtown, Ill.

[73] Assignee: Peter M. Bonutti, Effingham, Ill.

[21] Appl. No.: 297,258

[22] Filed: Aug. 26, 1994

Related U.S. Application Data

[62] Division of Ser. No. 126,081, Sep. 23, 1993, Pat. No. 5,395,303, which is a division of Ser. No. 690,845, Apr. 24, 1991, Pat. No. 5,285,773, which is a continuation-in-part of Ser. No. 559,700, Jul. 30, 1990, Pat. No. 5,167,612, which is a continuation-in-part of Ser. No. 686,811, Apr. 17, 1991, Pat. No. 5,213,094.

[51] Int. Cl.$^6$ ...................................................... A61F 5/00
[52] U.S. Cl. ................... 602/16; 602/20; 602/23; 601/33; 128/898
[58] Field of Search ............................ 602/5, 16, 20, 602/23, 26, 32, 36–38; 482/124, 130, 139; 601/23, 33, 34, 40; 128/898

[56] References Cited

U.S. PATENT DOCUMENTS

| | | |
|---|---|---|
| 3,814,419 | 5/1974 | Bjorklund et al. |
| 3,976,057 | 8/1976 | Barclay. |
| 4,039,183 | 8/1977 | Sakurada. |
| 4,180,870 | 1/1980 | Radulovic et al. |
| 4,214,577 | 7/1980 | Hoy. |
| 4,229,001 | 10/1980 | Roman. |
| 4,237,873 | 12/1980 | Terry et al. |
| 4,273,113 | 6/1981 | Hofstein. |
| 4,441,489 | 4/1984 | Evans et al. |
| 4,456,002 | 6/1984 | Barber et al. |
| 4,502,681 | 3/1985 | Blomqvist. |
| 4,508,111 | 4/1985 | Hepburn. |
| 4,509,509 | 4/1985 | Bouvet et al. |
| 4,538,595 | 9/1985 | Hajianpour. |
| 4,538,600 | 9/1985 | Hepburn. |
| 4,606,542 | 9/1986 | Segal. |
| 4,612,919 | 9/1986 | Best. |
| 4,665,905 | 5/1987 | Brown. |
| 4,718,665 | 1/1988 | Airy et al. |
| 4,790,301 | 12/1988 | Silfverskiold. |
| 4,848,326 | 7/1989 | Lonardo. |

(List continued on next page.)

FOREIGN PATENT DOCUMENTS

| | | |
|---|---|---|
| 0181688 | 5/1986 | European Pat. Off. |
| 0380060 | 8/1990 | European Pat. Off. |
| 2829562 | 7/1978 | Germany. |
| 806231 U | 5/1988 | Germany. |
| 1426580 | 9/1988 | U.S.S.R. |
| WO8804543 | 6/1988 | WIPO. |

OTHER PUBLICATIONS

Publication by Dynasplit Systems, Inc. entitled "Dynasplint LPS Orthosis–Knee Extension" (Date unknown, but prior to Aug. 23 1991).

Primary Examiner—Linda C. M. Dvorak
Attorney, Agent, or Firm—Tarolli, Sundheim & Covell

[57] ABSTRACT

An orthosis for stretching tissue that limits compressive forces on the soft tissue around a joint during movement of the joint. The orthosis includes two relatively pivotable cuff arms with a cuff on each arm. The cuffs clamp onto the body portions on either side of the joint. The pivot axis of the cuff arms is spaced from the pivot axis of the joint, so that movement of the cuff arms to extend the joint results in distractive forces being applied to the joint. The cuffs are selectively moved on the cuff arms, during extension and flexion, to provide the proper amount of distractive forces to the joint and to limit compressive forces on the joint. A mechanical advantage is gained through the use of a gear drive mechanism for transmitting to the joint the force applied by the patient. This allows the orthosis to be relatively small and light weight. The orthosis also provides a portable system for continuous passive motion therapy for a joint. The orthosis may be operated by a manual plus electric drive cycling it between extremes of motion. Provision is made for monitoring the range of motion or the force applied.

148 Claims, 10 Drawing Sheets

U.S. PATENT DOCUMENTS

| | | |
|---|---|---|
| 4,884,454 | 7/1989 | Rogers . |
| 4,930,497 | 6/1990 | Saringer . |
| 4,953,543 | 9/1990 | Grim et al. . |
| 4,955,369 | 9/1990 | Bledsoe et al. . |
| 5,018,514 | 5/1991 | Grood et al. . |
| 5,025,782 | 6/1991 | Salerno . |
| 5,027,688 | 7/1991 | Suzuki et al. . |
| 5,036,837 | 8/1991 | Mitchell et al. . |
| 5,102,411 | 4/1992 | Hotchkiss et al. . |
| 5,232,435 | 8/1993 | Leibinsohn . |

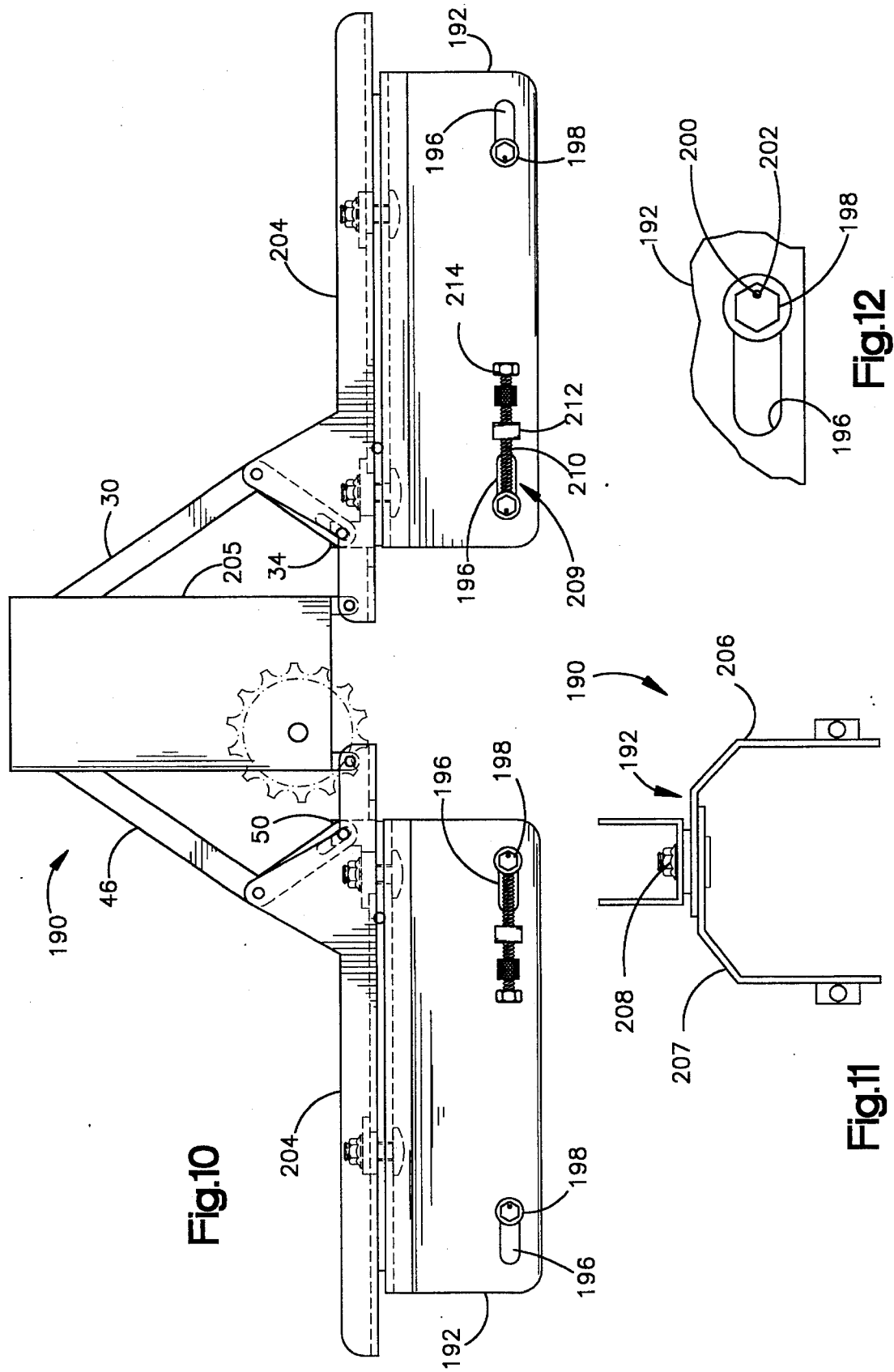

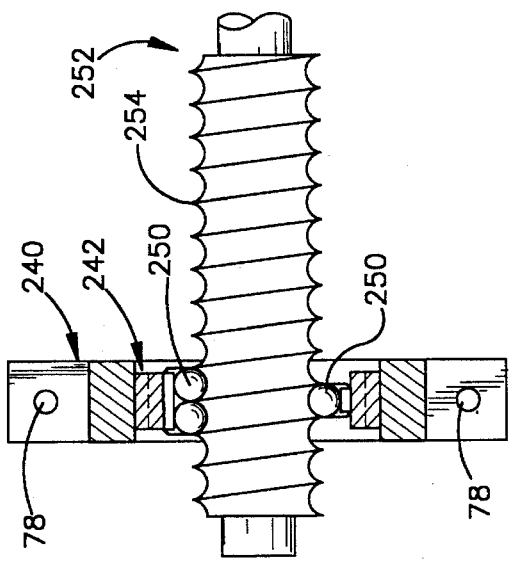
Fig.17
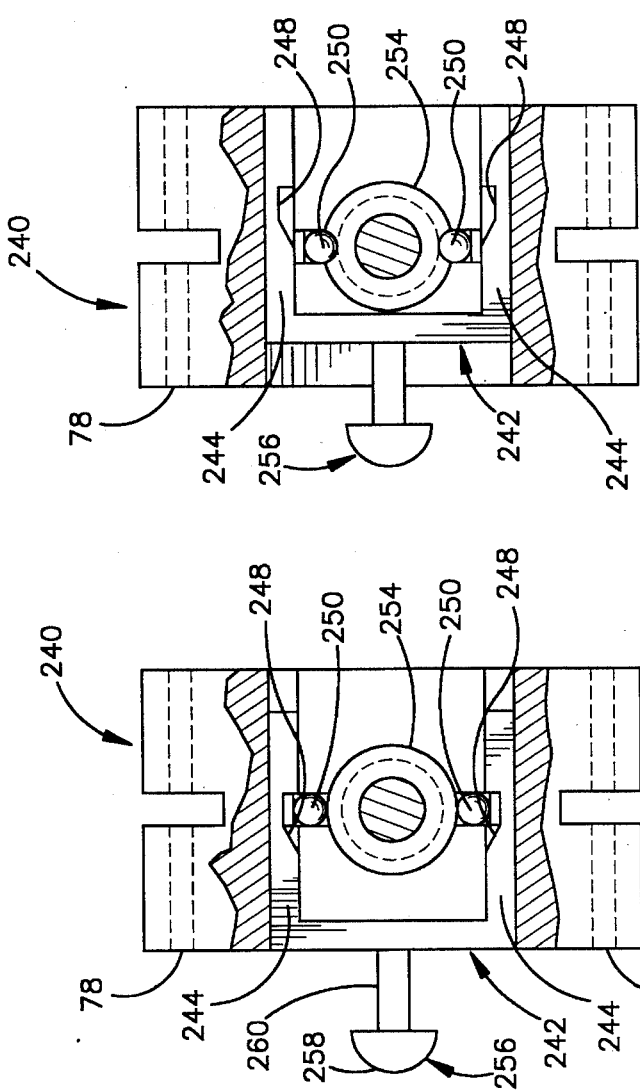
Fig.16
Fig.15
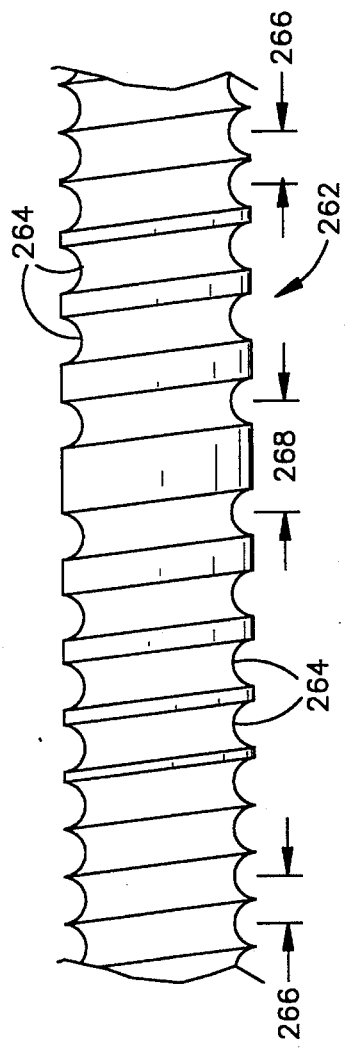
Fig.18

ORTHOSIS WITH DISTRACTION THROUGH RANGE OF MOTION

RELATED APPLICATIONS

This application is a divisional of application Ser. No. 08/126,081 filed Sep. 23, 1993, (now U.S. Pat. No. 5,395,303). The aforementioned application Ser. No. 08/126,081 is itself a divisional of application Ser. No. 07/690,845 filed Apr. 24, 1991, (now U.S. Pat. No. 5,285,773). The aforementioned application Ser. No. 07/690,845 is itself a continuation-in-part of application Ser. No. 07/559,770 filed Jul. 30, 1990, (now U.S. Pat. No. 5,167,612). The aforementioned application Ser. No. 07/690,845 is also a continuation-in-part of application Ser. No. 07/686,811, filed Apr. 17, 1991, (now U.S. Pat. No. 5,213,094). The benefit of the earlier filing dates of the aforementioned applications Ser. Nos. 08/126,081; 07/690,845; 07/559,700 and 07/686,811 is claimed for all common subject matter.

BACKGROUND OF THE INVENTION

1. Technical Field

The present invention relates to an orthosis for stretching tissue in the human body to regain joint motion and eliminate tissue contracture. In particular, the present invention relates to an orthosis which limits compressive forces on the soft tissue around a joint while it stretches tissue around a joint. The present invention also relates to a continuous passive motion system for joint therapy.

2. Description of the Prior Art

When the full range of movement of a joint is not available, such as after surgery or trauma, tissue around the joint stiffens and loses its ability to move through the extremes of motion. Various devices have been designed to regain range of motion.

U.S. Pat. No. 4,612,919 shows an adjustable limb support for adjustably orienting the forearm and upper arm of a human patient in a variety of angular relationships to therapeutically treat the contracted muscles in the patient's arm.

U.S. Pat. No. 4,848,326 shows a knee contracture correction device for straightening a contracted knee.

U.S. Pat. No. 4,538,600 shows an adjustable splint assembly with a lower strut and an upper strut pivotably connected to the lower strut. An internal spring applies a force at the pivot point to align the upper and lower struts to straighten the limb to which the splint is attached. A similar device is also shown in U.S. Pat. No. 4,508,111. Similar devices are in use and are sold under the trademark DYNASPLINT by Dynasplint Systems, Inc.

U.S. Pat. No. 4,665,905 shows a dynamic elbow and knee extension device with a centrally positioned compression spring.

It is also known in the art to put a rigid element including a turnbuckle, on the inside angle of a joint, between two cuffs attached to limb segments and use the turnbuckle to vary the length of the rigid element to pull and push the limb segments relative to each other. It has been found that this device does not work very well in practice because it is cumbersome and difficult to obtain relatively full extension or flexion at the extremes of motion.

Each of the above-identified prior art devices, and each of the devices in use at the present time, does not apply adequate force in the appropriate planes. Further, each of these devices applies undesirable compressive forces on the soft tissues around a joint upon flexion and extension of the joint. None allows the patient to provide the proper therapy by himself, without the assistance of a therapist who manually stretches the joint. None allows the patient to control the therapy process in a self-directed manner.

Accordingly, it is desirable to provide a self-directed therapy device which not only enhances the range of motion of the joint but also limits compressive joint forces, distracts the joint and stretches soft tissue. "Distraction" is defined by one dictionary as "Separation of the surfaces of a joint by extension without injury or dislocation of the parts." (*Taber's Cyclopedic Medical Dictionary*, 16th Edition, 1989, page 521), and involves stretching rather than compressing the joint capsule, soft tissue, ligaments, and tendons.

The device should limit tissue damage by controlling the amount of force applied, and should apply a progressive gradual stretching action and have a locking mechanism to maintain a joint in a selected position, because tissue is viscoelastic. This is the best way to establish or reestablish a range of motion in the soft tissues around a joint, as it does not involve damaging the tissue.

An orthosis should also be lightweight and portable so that it can be used in a seated, upright, or functional position. This should be the case for both a stretching device and a continuous passive motion (CPM) device.

SUMMARY OF THE INVENTION

In the earlier filed co-pending applications identified above, there were disclosed orthoses having certain novel features and advantages. The present invention is an improved version of the earlier orthoses.

As in the earlier orthoses, a tower provides mechanical advantage for increasing the range of motion of the joint. A significant mechanical advantage is also gained through the use of a gear drive mechanism for transmitting to the joint the force applied by the patient. This allows the orthosis to be relatively small and light weight. This mechanical advantage can also be achieved through the use of drive mechanisms other than the gear drive. In any case, the drive mechanism can deliver appropriate force or greater force to stretch soft tissue.

In the present invention, the orthosis provides for distraction of the joint through the entire range of motion. The orthosis includes two relatively pivotable cuff arms. Each cuff arm has a cuff mounted on the cuff arm. The cuffs clamp onto the body portions on either side of the joint. The pivot axis of the cuff arms is spaced from the pivot axis of the joint. Movement of the cuff arms to extend the joint results in distractive forces being applied to the joint. These distractive forces are limited and controlled by having the cuffs slidable on the cuff arms. The cuffs are selectively moved along the cuff arms, during relative movement of the cuff arms, to provide the proper amount of distractive forces to the joint and to limit compressive forces on the joint. Thus, the orthosis is well suited for stretching therapy.

The orthosis may also provides an optional system for continuous passive motion therapy for a joint. The orthosis is light weight and may be operated by an electric motor cycling it between flexion and extension. This may also be done in combination with the manual stretching therapy.

BRIEF DESCRIPTION OF THE DRAWINGS

The foregoing and other features of the present invention will become apparent to one skilled in the art upon a consideration of the following description of the invention with reference to the accompanying drawings, wherein:

FIG. 10 is a view similar to FIG. 1 of an orthosis having structure for adjusting longitudinal placement of the cuffs relative to the body portions;

FIG. 11 is an end view of the orthosis of FIG. 10 showing structure for adjusting the width of a cuff;

FIG. 12 is an enlarged view of a portion of the orthosis of FIG. 10 showing structure for adjustably receiving a pin or K-wire;

FIG. 15 is a top plan view of an arm actuator block that is disengageable from a ball thread lead screw, in an engaged condition;

FIG. 16 is a view similar to FIG. 16, with the arm actuator block in a disengaged condition;

FIG. 17 is a front elevational of the lead screw and arm actuator block of FIG. 15;

FIG. 18 is a schematic front elevational of a variable pitch lead screw.

DESCRIPTION OF PREFERRED EMBODIMENTS OF THE INVENTION

Figure 1:
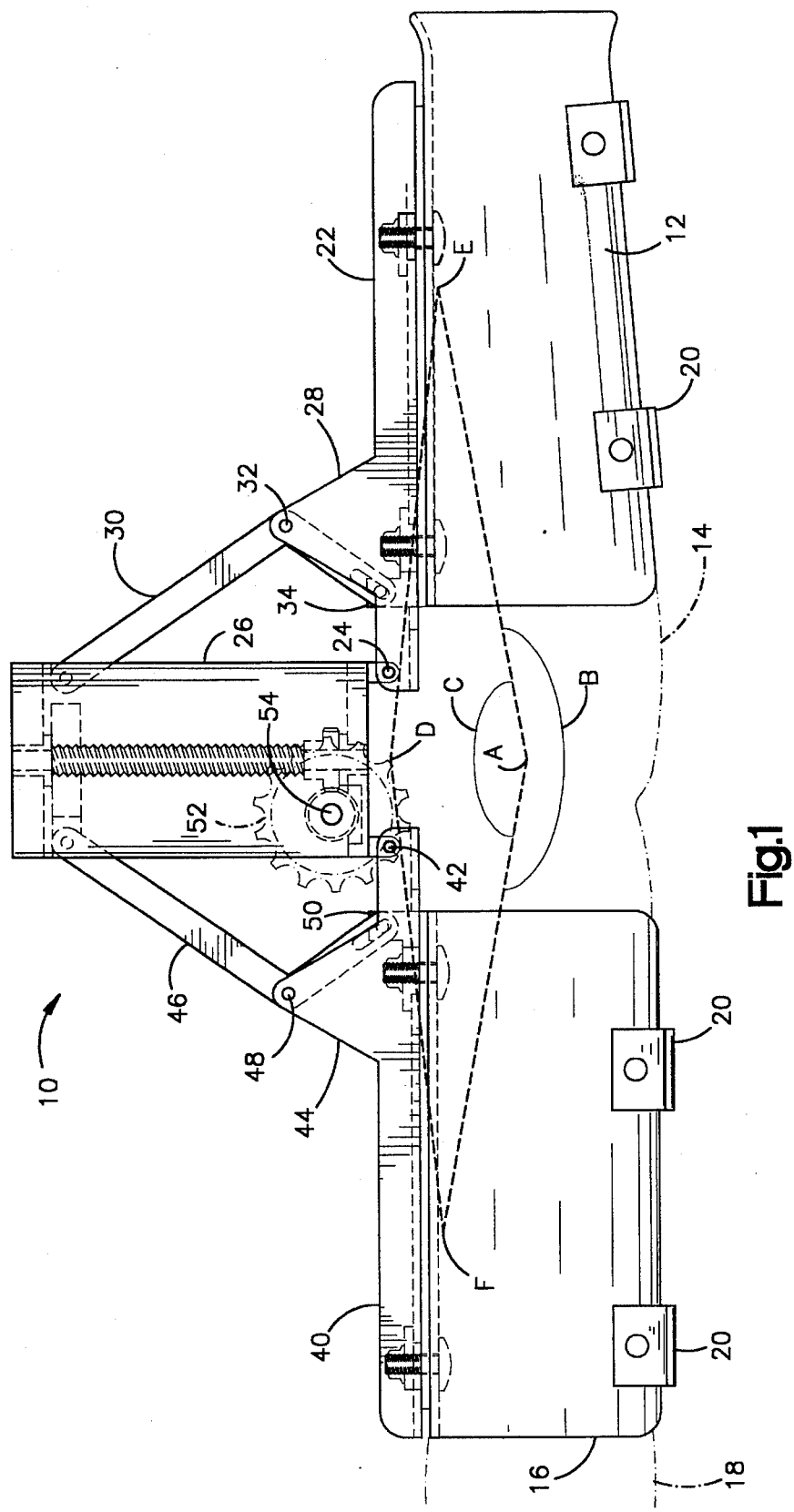
FIG. 1 is a view of an orthosis in accordance with the present invention.

The present invention relates to an orthosis and particularly to an orthosis for moving a joint between first and second relatively movable body portions. The present invention is applicable to various orthosis constructions. As representative of the present invention, FIG. 1 illustrates generally an orthosis 10. In FIG. 1 the orthosis 10 is illustrated as attached to a human arm, for moving the elbow joint which is between the upper arm and the forearm.

It should be understood that the orthosis 10 can be used to extend or flex other joints in the body, such as a knee joint or a wrist joint or ankle joint, with the construction of the orthosis 10 in such case being varied to fit the particular application. The orthosis can be used, for example, to flex the ankle joint to stretch a tight achilles tendon in cerebral palsy or post traumatic contractures. It is especially useful in obtaining the last degrees of joint extension. The orthosis can be custom made to fit a particular individual, or can be an off the shelf item. The orthosis can also be used, for example, to eliminate contractures or stress soft tissue. It can be used for patients with cerebral palsy, stroke, spastic paralysis, as well as in post-traumatic or post-surgical cases. It can also be used, for example, in therapy after a knee replacement, in which the extremes of motion in extension or flexion are difficult to obtain without extensive intervention of a therapist.

The orthosis 10 includes a first cuff 12 for attachment to a first body portion 14 such as the forearm, and a second cuff 16 for attachment to a second body portion 18 such as the upper arm. (The term "cuff" as used herein means any suitable structure for transmitting the force of the orthosis to the limb portion it engages.) The first body portion 14 is joined to the second body portion 18 at the elbow joint designated A, around which is located, as is well known, soft tissue. Each of the first and second cuffs 12 and 16 includes a plurality of loop connectors 20 for receiving straps extending around the body portions 14 and 18 to clamp the cuffs 12 and 16 to the body portions 14 and 18.

The first cuff 12 is mounted for sliding movement on a first cuff arm 22. (The term "cuff arm" as used herein means any suitable structure for transmitting the force of the orthosis to the cuff and thence to the limb portion.) The first cuff arm 22 is pivotally mounted by a pin 24 to a tower 26. The first cuff arm 22 includes a support 28. A first lever arm 30 extends from the tower 26 and is pivotally connected to the support 28 by a pin 32. The first lever arm 30 is pivotally connected to a cuff actuator block 34. The cuff actuator block 34 is fixed to the first cuff 12 and is slidable along the first cuff arm 22 in a manner as described below.

The second cuff 16 is mounted for sliding movement on a second cuff arm 40. The second cuff arm 40 is pivotally mounted by a pin 42 to the tower 26. The second cuff arm 40 includes a support 44. A second lever arm 46 extends from the tower 26 and is pivotally connected to the support 44 by a pin 48. The second lever arm 46 is pivotally connected to a cuff actuator block 50. The cuff actuator block 50 is fixed to the second cuff 16 and is slidable along the second cuff arm 40 in a manner as described below.

The tower 26 is a box-like structure including a lower housing 66 and an upper housing 70 joined by a front plate 51 and a back plate 53. A drive mechanism for the orthosis 10 is disposed substantially within the tower 26. The drive mechanism includes a manually actuatable knob 52 (FIG. 1) which is fixed to a shaft 54. The shaft 54 extends into the tower 26 and a gear 56 (FIG. 2) is fixed to the shaft. The gear 56 engages external gear teeth 58 on a gear 60. Rotation of the gear 56 about its axis causes rotation of the gear 60 about its axis.

The gear 60 is fixed to an externally threaded lead screw 62. One end of the lead screw 62 is journalled for rotation in a bushing 64 mounted in a lower housing 66 of the tower 26. The Opposite end of the lead screw 62 is journalled for rotation in a bushing 68 mounted in an upper housing 70 of the tower 26. An arm actuator block or base link 72 has an internally threaded opening 74 through which the lead screw 62 extends in threaded engagement. As the lead screw 62 rotates, the actuator block moves axially along the lead screw 62 within the tower 26.

A pin 76 is fixed in the arm actuator block 72. The pin 76 extends through an opening 78 in a first portion 80 of the first lever arm 30. The first lever arm 30 is L-shaped, having an elbow portion 82 intermediate the first portion 80 and a second portion 84. An opening 86 extends through the elbow portion 82 of the first lever arm 30. A pin 88 fixed in the support 28 of the first cuff arm 22 extends through the opening 86. A slot 90 extends through the second portion 84 of the first lever arm 30.

Figure 4:
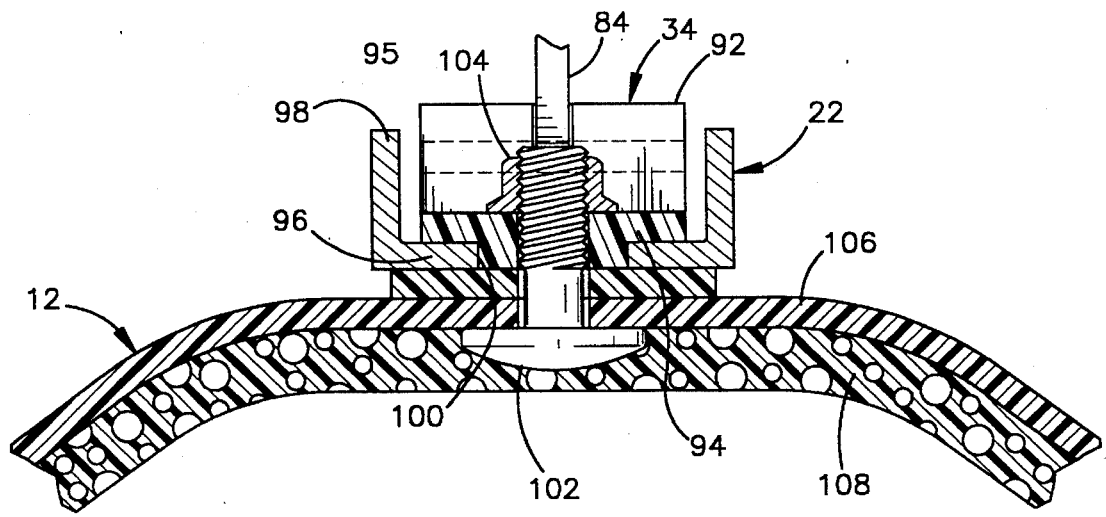
FIG. 4 is a sectional view through a cuff attachment point including the cuff actuator block.

The cuff actuator block 34 (FIG. 4) includes a pin portion 92 and a guide portion 94. The pin portion 92 has an open center and receives therein the slotted second portion 84 of the first lever arm 30. A pin 95 having its ends fixed in the pin portion 92 extends through the slot 90 in the lever arm portion 84, thus connecting the first lever arm 30 to the cuff actuator block 34.

Each cuff arm functions as a track along which its respective cuff slides. Each cuff arm may thus take any suitable shape. In a preferred embodiment, the cuff arms are U-shaped and include a bottom portion and upstanding side portions. Thus, the first cuff arm 22 is U-shaped and includes a bottom portion 96 and a side portion 98. Part of the guide portion 94 of the cuff actuator block 34 is supported on the bottom portion 96 of the first cuff arm 22. Part of the guide portion 94 is received in a slot 100 in the first cuff arm 22.

A bolt 102 extends through the slot 100 and with a nut 104 secures the cuff actuator block 34 to the shell 106 of the first cuff 12. The nut 104 is turned down only tightly enough to secure the cuff actuator block 34 for movement with the cuff shell 106, while allowing the shell 106 to slide relative to the first cuff arm 22. The head of the bolt 102 is within a layer 108 of padding on the inside of the shell 106.

Figure 3:
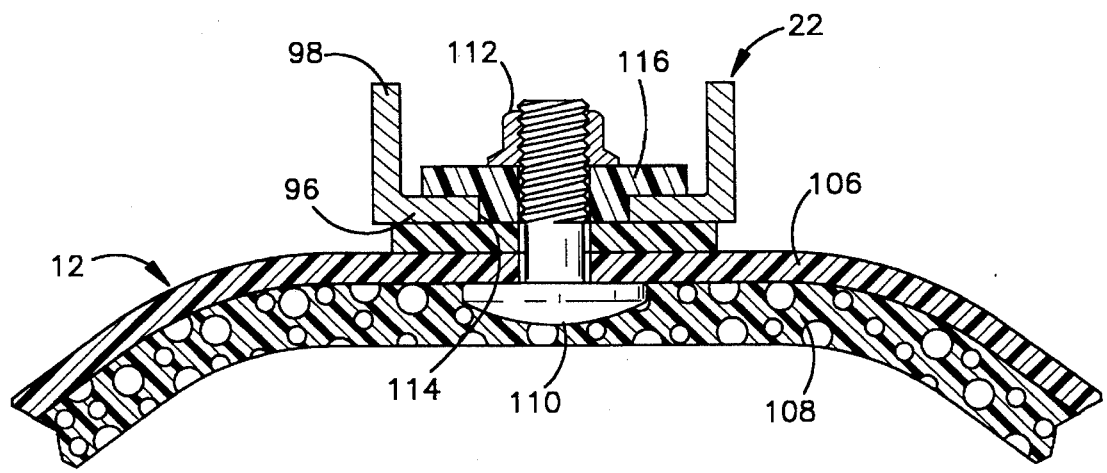
FIG. 3 is a sectional view through a cuff attachment point.

The first cuff 12 is also slidably mounted to the first cuff arm 22 at a second location (FIGS. 3 and 5) by a bolt 110 and a nut 112. The bolt 110 extends through a slot 114 in the bottom portion of the first cuff arm 22 and through a bearing 116 which mounts the first cuff 12 for sliding movement relative to the first cuff arm 22. Again, the nut 112 is turned down only tightly enough to secure the bearing 116 for sliding movement with the shell 106, while allowing the shell 106 to slide relative to the first cuff arm 22.

The second cuff 16 is similar to the first cuff 12, differing in the illustrated embodiment only in that it is shorter to fit the second body portion 16 rather than the first body portion 14. Similarly, the second cuff arm 40 is similar to the first cuff arm 22, differing in the illustrated embodiment only in that it is shorter to fit the shorter second cuff 16. It should be understood that the cuffs are, in any particular embodiment, sized to fit the particular body portion (leg, arm, ankle, etc.) to which they are to be connected. Accordingly, the illustration of the second cuff being shorter than the first cuff is only in one particular application and is not to be considered limiting in any regard. All the other parts of the drive mechanism, etc. are similar between the two sides of the orthosis.

In accordance with a feature of the present invention, the pivot point of the cuff arms 22 and 40 is spaced outwardly from the joint A, so that the joint A can be distracted. The first body portion 14, the joint A, and the second body portion 16 define on one side of the joint A an inner sector "B" (inside the bend of the limb) which decreases in angle as the joint A is flexed (bent). The first body portion 14, the joint A, and the second body portion 16 define on the opposite side of the joint A an outer sector "C" which decreases in angle as the joint A is extended (straightened). The tower 26 is located in the outer sector "C".

The pivot axis of the cuff arms is represented by the point D in the outer sector C (see FIG. 1). The distance between the point D and a point E on the first cuff arm 22 is the same as the distance between the point D and a point F on the second cuff arm 40. The dotted line triangles in FIG. 1 illustrate the relative positions of the various points in FIG. 1.

Assuming that the first body portion 14 were securely fixed to the first cuff arm 22 by the first cuff 11, and that the second body portion 18 were securely fixed to the second cuff arm 40 by the second cuff 16, then upon rotation of the cuff arms relative to each other from a more flexed position to a more extended position, the points E and F would move upwardly as viewed in FIG. 1. Since the distance between the points A and D would not change, then the joint A would be subjected to distractive forces tending to pull the joint A apart.

It can thus be seen that, because the pivot point D of the cuff arms 22 and 40 is spaced outwardly from the joint A, when the orthosis 10 is extended, the joint A is distracted. Thus, the tower 26 provides a triangular or tripod effect and also serves to provide an increased moment arm for the first and second lever arms 30 and 46.

Such distraction of the joint is desirable, as noted above. However, it has been found an excessive amount of distractive force can be applied in this manner. Accordingly, in the orthosis 10 according to the present invention, the amount of distraction is controlled in a manner described below.

Extension

In operation of the orthosis illustrated in FIGS. 1–5, the knob 52 is rotated by the application of an external force. The knob 52 is fixed to the shaft 54 and the gear 56, and thus the gear 56 rotates. The gear 56 causes the gear 60 to rotate. The gear 60 is fixed to the lead screw 62, and thus the lead screw 62 rotates. Rotation of the lead screw 62 results in axial movement of the arm actuator block 72. The gearing provides a substantial mechanical advantage in the operation of the drive mechanism. The gear ratios may be selected to give the desired amount of cuff arm movement for a given amount of force input to the orthosis.

Figure 5:
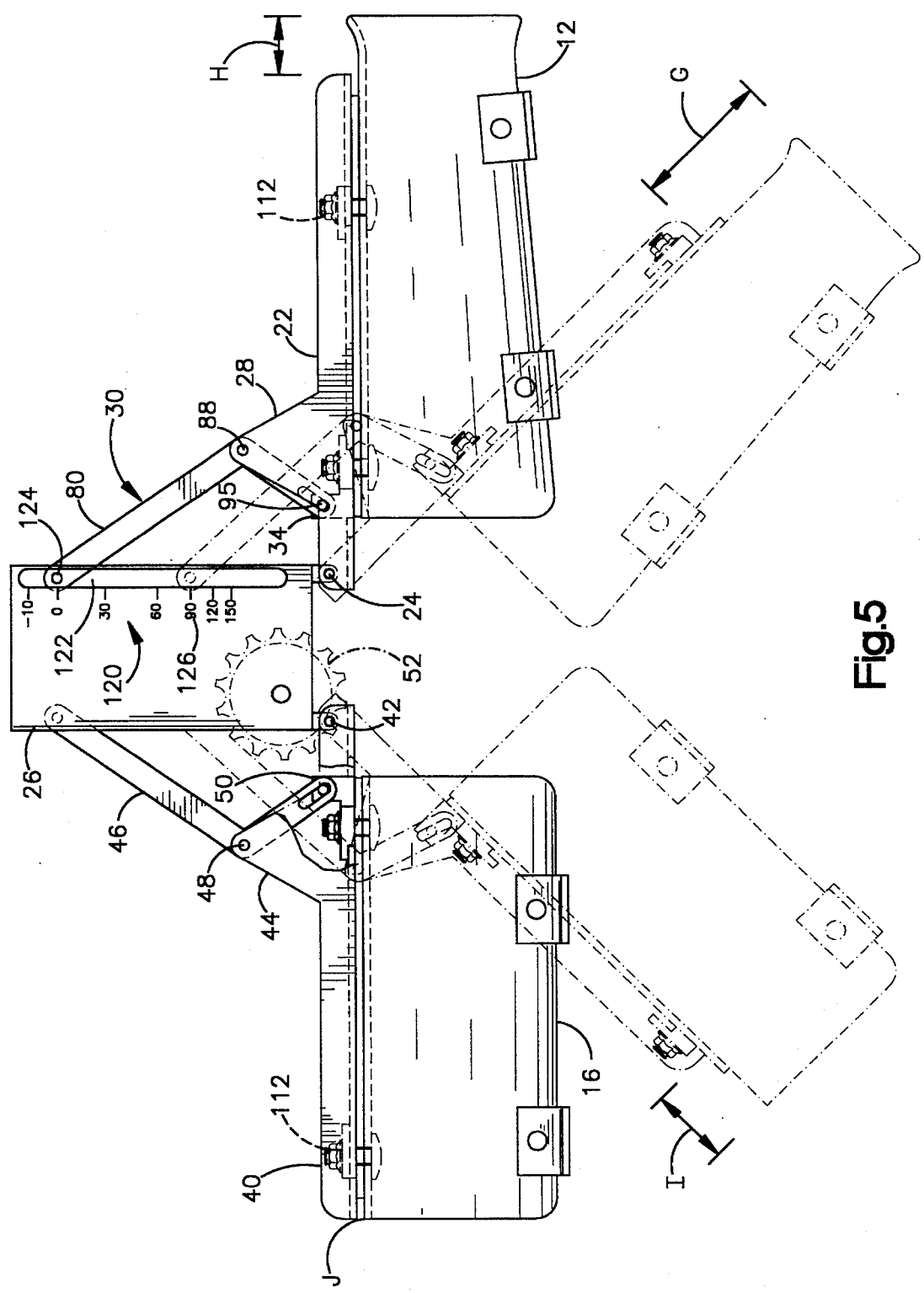
FIG. 5 is a view showing the orthosis of FIG. 1 in two positions of its range of motion.

In operation of the orthosis 10 to extend the joint, the orthosis 10 starts at a more flexed position such as the position shown in dashed lines in FIG. 5. The first and second cuffs 12 and 16 are clamped onto the first and second body portions 14 and 18 (FIG. 1), respectively, by straps through the loops 20, tightly enough so that the cuffs 12 and 16 can apply torque to the body portions 14 and 18 to extend the joint A.

Figure 2:
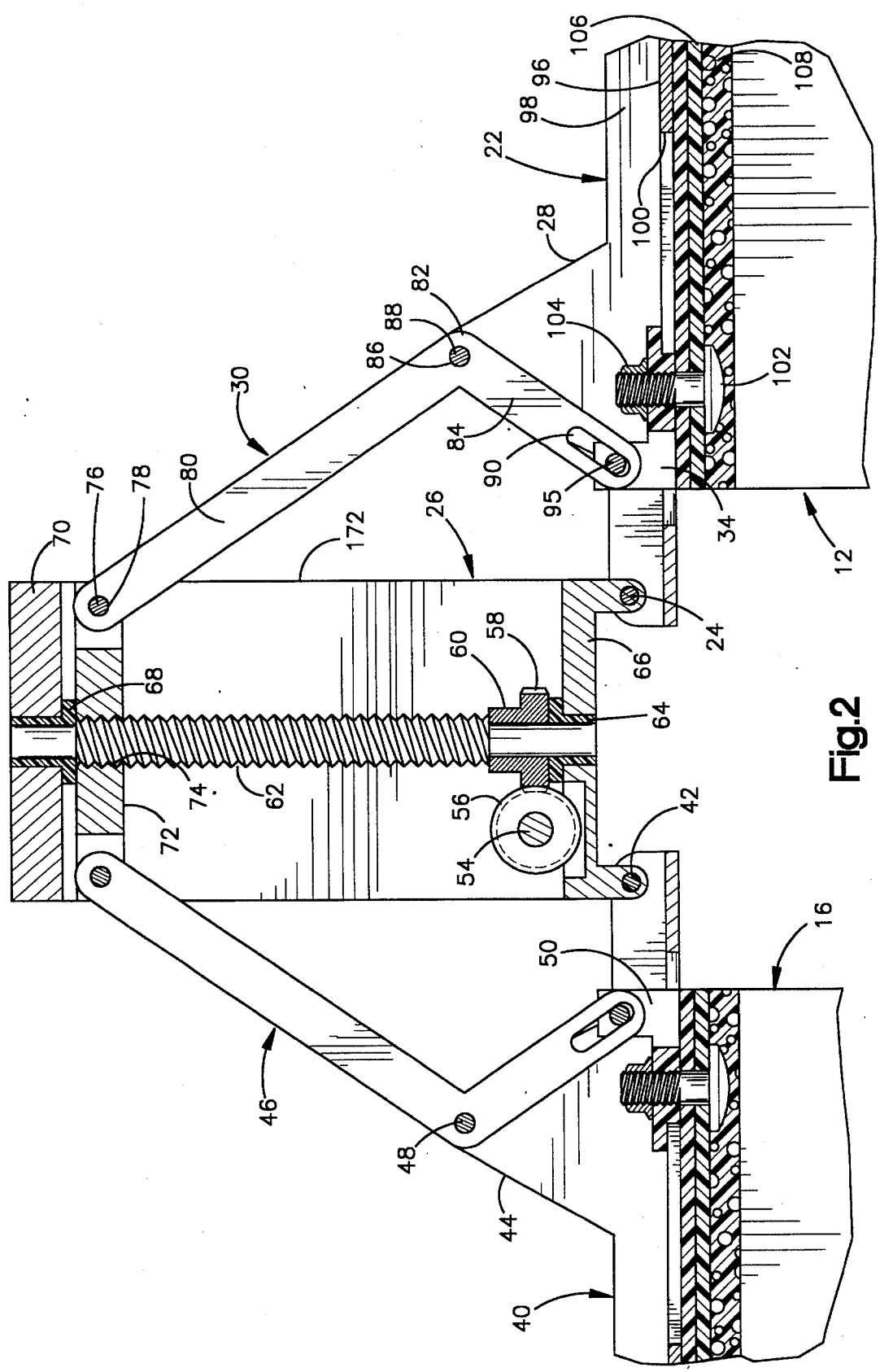
FIG. 2 is an enlarged sectional view of a portion of the orthosis of FIG. 1 including the drive mechanism.

The knob 52 is turned so that the arm actuator block 72 moves upward as viewed in FIGS. 2 and 5, that is, toward the upper housing 66. As the arm actuator block 72 moves upward, it moves the pin 76 upward also. The pin 76 applies an upwardly-directed force on the first portion 80 of the first lever arm 30. This force is transmitted to and through the pin 88, the support 28, and to the first cuff arm 22. The first cuff arm 22 pivots about the pin 24, toward the position shown in solid lines in FIG. 2.

The first lever arm 30 also applies an upwardly-directed force on the pin 95 fixed to the cuff actuator block 34. As the first cuff arm 22 pivots relative to the tower 26, the cuff actuator block 34, because it can slide along the first cuff arm 22, moves inwardly along the first cuff arm 22. The first cuff 12, which is fixed to the cuff actuator block 34, also moves inwardly along the first cuff arm 22. This can be seen clearly in FIG. 5 by comparing the distance marked G, to the distance marked H. The distance marked G is the distance between the end of the first cuff 12 and the end of the first cuff arm 22 when the orthosis is in a relatively flexed condition. The distance marked H is the distance between the end of the first cuff 12 and the end of the first cuff arm 22 when the orthosis is in a relatively extended condition. The distance marked G is greater than the distance marked H.

The operation with respect to the second cuff arm 40 is similar. As the arm actuator block 72 moves upward, it applies an upwardly-directed force on the second lever arm 46. This force is transmitted to and through the support 44 to the second cuff arm 40. The second cuff arm 40 pivots about the pin 42, toward the position shown in solid lines in FIG. 2.

The second lever arm 46 also applies an upwardly-directed force on the cuff actuator block 50. As the second cuff arm 40 pivots relative to the tower 26, the cuff actuator block 50, because it can slide along the second cuff arm 40, moves inwardly along the second cuff arm 40. The second cuff 16, which is fixed to the cuff actuator block 50, also moves inwardly along the cuff arm 40. This can be seen clearly in FIG. 5 by comparing the distance marked I to the distance marked J. The distance marked I is the distance between the end of the second cuff 16 and the end of the second cuff arm 40 when the orthosis is in a relatively flexed condition. The distance marked J is the distance between the end of the second cuff 16 and the end of the second cuff arm 40 when the orthosis is in a relatively extended condition. The distance marked I is greater than the distance marked J.

Because the cuffs are clamped onto the first and second body portions as described above, the outward pivoting movement of the cuff arms and the cuffs causes the joint to be extended as desired. However, this extension of the joint, as described above, can place strong distractive forces on the soft tissues around the joint. The sliding movement of the cuffs, inwardly along the cuff arms, helps to limit these distractive forces by counteracting the outward movement of the cuff arms. Preferably, the cuffs slide inwardly along the cuff arms a distance far enough so that the joint is only slightly distracted during extension. Thus, the detrimental effects of strong distractive forces normally generated in forced extension of a joint are avoided, being replaced with the beneficial effects of limited and controlled distraction.

Flexion

In operation of the orthosis 10 to flex a joint, the orthosis 10 starts at a more extended position such as the position shown in solid lines in FIG. 5. The first and second cuffs 12 and 16 are clamped onto the first and second body portions 14 and 18 (FIG. 1), respectively, by straps through the loops 20, tightly enough so that the cuffs 12 and 16 can apply torque to the body portions 14 and 18 to extend the joint A.

The knob 52 is turned so that the arm actuator block 72 moves downward as viewed in FIGS. 2 and 5, that is, toward the lower housing. As the arm actuator block 72 moves downward, it applies a downwardly-directed force on the first portion 80 of the first lever arm 30. This force is transmitted to and through the pin 88, the support 28, and to the first cuff arm 22. The first cuff arm 22 pivots about the pin 24, toward the position shown in dashed lines in FIG. 5.

The first lever arm 30 also applies a downwardly-directed force on the pin 95 fixed to the cuff actuator block 34. As the first cuff arm 22 pivots relative to the tower 26, the cuff actuator block 34, because it can slide along the first cuff arm 22, moves outwardly along the first cuff arm 22. The first cuff 12, which is fixed to the cuff actuator blocks 34, also moves outwardly along the first cuff arm 22. This can be seen clearly in FIG. 5 by comparing the distance marked G, to the distance marked H. The distance marked G is the distance between the end of the first cuff 12 and the end of the first cuff arm 22 when the orthosis is in a relatively flexed condition. The distance marked H is the distance between the end of the first cuff 12 and the end of the first cuff arm 22 when the orthosis is in a relatively extended condition. The distance marked G is greater than the distance marked H.

operation with respect to the second cuff arm 40 is similar. As the arm actuator block 72 moves downward, it applies a downwardly-directed force on the second lever arm 46. This force is transmitted to the second cuff arm 40. The second cuff arm 40 pivots about the pin 42 relative to the tower 26, toward the position shown in dashed lines in FIG. 2.

The second lever arm 46 also applies a downwardly-directed force on the cuff actuator block 50. As the second cuff arm 40 pivots relative to the tower 26, the cuff actuator block 50, because it can slide along the second cuff arm 40, moves outwardly along the second cuff arm 40. The second cuff 16, which is fixed to the cuff actuator block 50, also moves outwardly along the second cuff arm 40. This can be seen clearly in FIG. 5 by comparing the distance marked I to the distance marked J. The distance marked I is the distance between the end of the second cuff 16 and the end of the second cuff arm 40 when the orthosis is in a relatively flexed condition. The distance marked J is the distance between the end of the second cuff 16 and the end of the second cuff arm 40 when the orthosis is in a relatively extended condition. The distance marked I is greater than the distance marked J.

Because the cuffs are clamped onto the first and second body portions as described above, the inward pivoting movement of the cuff arms and thus the cuffs causes the joint to be flexed as desired. However, this flexion of the joint can place strong compressive forces on the soft tissues around the joint. The sliding movement of the cuffs, outwardly along the cuff arms, helps to limit these compressive forces by counteracting the inward movement of the cuff arms. Preferably, the cuffs slide outwardly along the cuff arms a distance far enough so that the joint is actually distracted somewhat during flexion. Thus, the detrimental effects of the compressive forces normally generated in forced flexion of a joint are avoided, being replaced with the beneficial effects of a controlled amount of distraction.

The orthosis in accordance with the present invention may include means for monitoring the angle between the first and second cuff arms 22 and 40. In one embodiment, this may be a goniometer 120 as illustrated in FIG. 5. A slot 122 extends along the length of the tower 26. A pin 124 on the first lever arm 30 is visible through the slot 122. The position of the pin 124 is readable against a scale 126 indicating degrees of flexion of the joint. As the first and second lever arms 30 and 46 pivot relative to each other, the first lever arm 30 moves downward in the tower 126. The pin 124 moves along the slot 122 and indicates the relative position of the two cuff arms 22 and 40. Equivalent manners of measuring the angle between the two arms are possible and are included within the scope of the invention.

An orthosis in accordance with the present invention may include means for adjusting the angle between a cuff arm and the cuff attached thereto. This can be used to apply an initial biasing force in one direction, or to position the limb portion initially within the cuff. This can also be used to accommodate angular displacement between the first and second body portions. For example, in an elbow joint there is normally about a 7° angle between the upper arm and the forearm.

Figure 7:
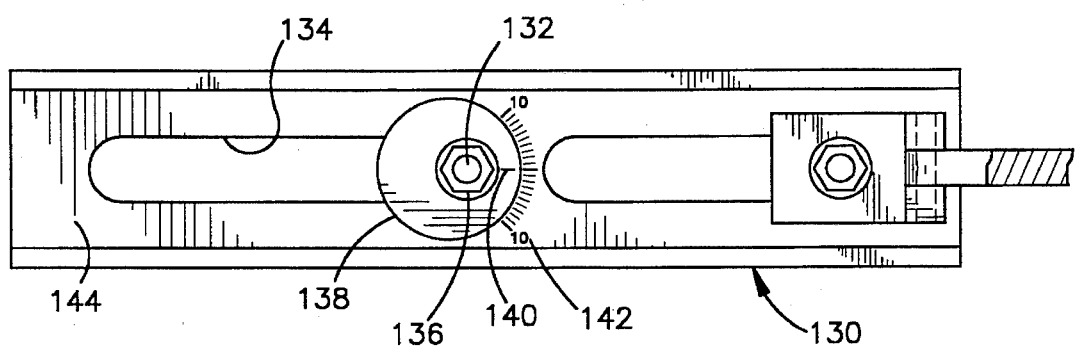
FIG. 7 is a view of a structure for varying angular attachment of the cuffs to the cuff arms.

In one embodiment, this may be a mechanism as illustrated in FIG. 7, which is a top plan view of a portion of a cuff arm 130. A cuff attachment screw 132 is movable in a slot 134 and can be slidably fixed in position with a nut 136, as in the embodiment of FIGS. 1–5. However, the opening in the bearing 138 through which the screw 132 extends is off-center of the bearing 138. Also, the bearing 138 has a marker 140 readable against a scale 142 on the bottom portion 144 of the cuff arm 130. Rotation of the bearing 138 in the slot 134 moves the screw 132 off the longitudinal center line of the cuff arm 130. This causes the cuff (not shown in FIG. 7) fixed to the screw 132 to be rotated with respect to the cuff arm 130. The cuff can then be fixed in a given angular orientation relative to the cuff arm 132. Equivalent manners of setting an angular orientation between a cuff and its cuff arm are possible and we included within the scope of the invention.

Figure 6:
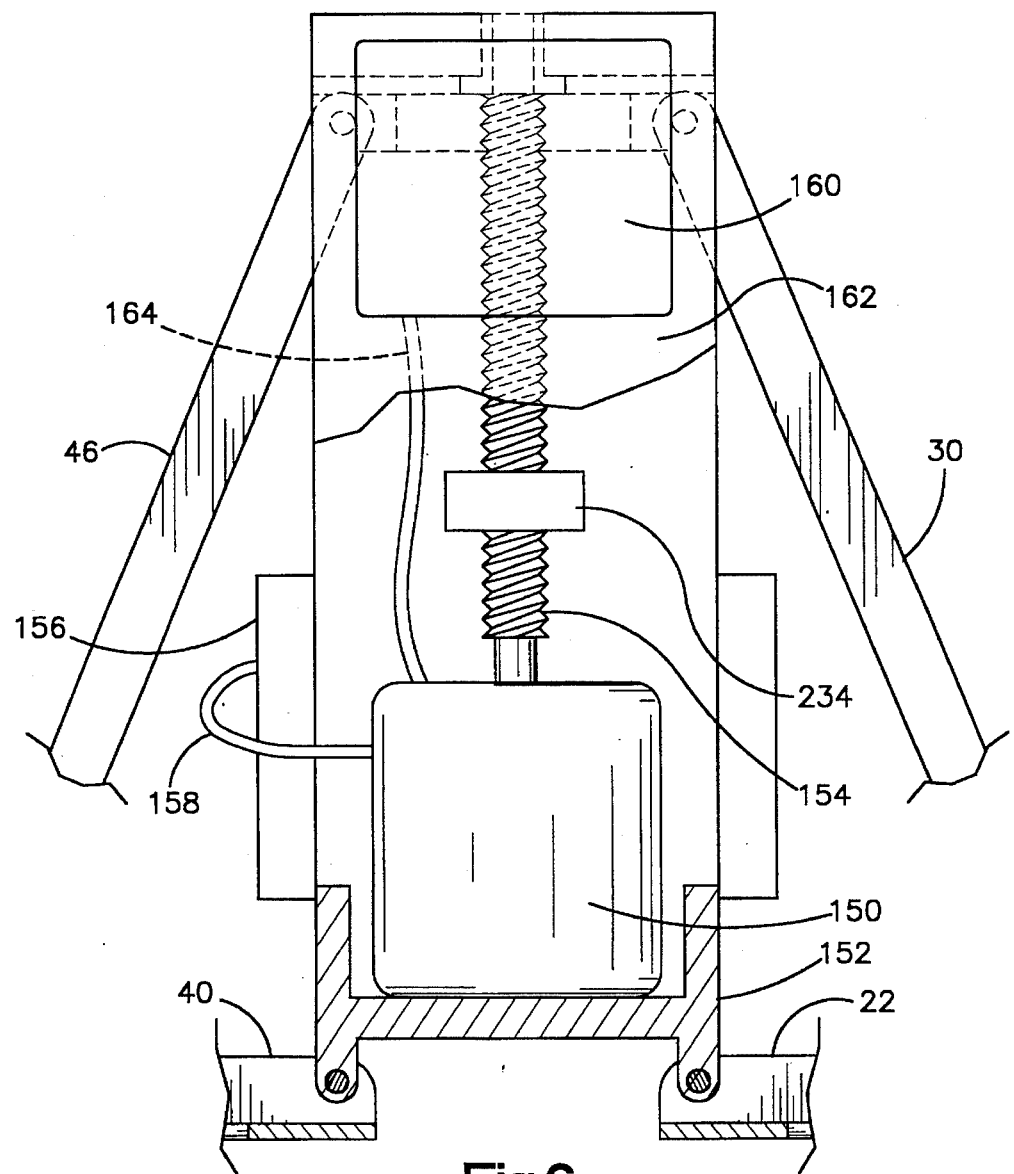
FIG. 6 is a view of an orthosis having an electric motor drive.

The drive mechanism for an orthosis in accordance with the present invention can be actuated by an electric motor instead of by a manually actuatable member such as the knob 52. FIG. 6 illustrates one way of utilizing an electric motor for this purpose.

In FIG. 6, an electric motor 150 is mounted in the lower portion of a tower 152. The motor 150 is drivingly connected to a lead screw 154. The lead screw 154 moves the lever arms 30 and 46 in the same manner as in the embodiment of FIGS. 1–5. The lever arms 30 and 46 move the cuff arms 22 and 40 in the same manner as in the embodiment of FIGS. 1–5.

A battery 156 secured to the back plate of the tower 152 provides electric power to the motor 150 through wires 158. Alternatively, the motor could be supplied with external power. A microprocessor indicated schematically at 160 and mounted on the front plate 162 of the tower 152 controls the operation of the motor 150 through signals sent along wires 164. The microprocessor 160 and motor 150 together can be used to cycle the cuff arms 22 and 40 through extension and flexion; to move the cuff arms 22 and 40 in one pivotal direction a certain amount, hold there while tissue stretches, then move further in that direction; or in any other manner. In another manner of use, the orthosis can be set to cycle to one end of the joint's range of motion and hold there for a predetermined period of time, then cycle to the other end of the joint's range of motion and hold there. The programming and control of the microprocessor 160 is within the skill of the art as it relates to driving the motor to control the cuff arms 22 and 40 to move in known manners. This embodiment is ideally suited for continuous passive motion exercise, because the orthosis is portable and because the motor can be programmed with the desired sequence of movements.

It should be understood that the particular physical arrangement of the motor 150, the battery 156, and the microprocessor 160, which is illustrated and described herein, is not the only possible arrangement of those elements. The invention contemplates that other arrangements of these or similarly functional elements are quite suitable, and thus, the invention is intended to cover any such arrangement.

Figure 9:
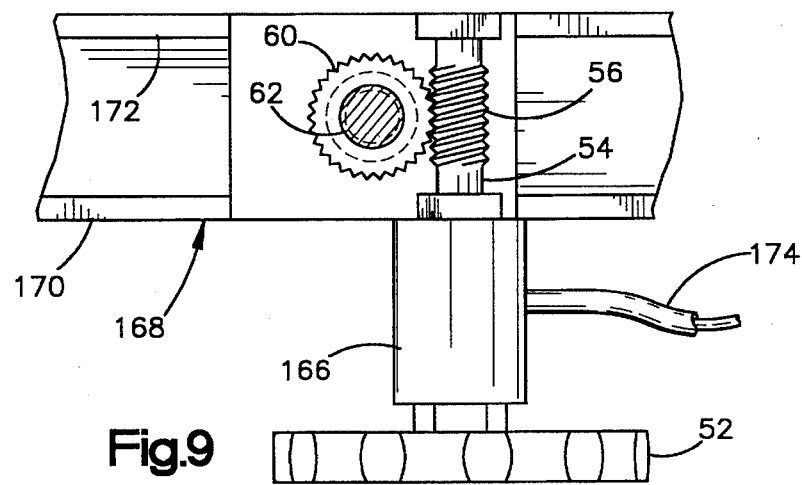
FIG. 9 is a plan view of an orthosis having an alternate electric drive, combined with a manual drive.

FIG. 9 illustrates an alternative method of using an electric motor drive. An electric motor 166 is mounted on the outside of a tower 168, on the front plate 170 of the tower 168. The motor 166 drives the shaft 54 which extends between the front plate 170 and the back plate 172 of the tower 168. The shaft 54 carries the gear 56, as in the embodiment of FIGS. 1–5. The motor 166 is supplied with electric power, and control signals, through wires 174. A manually actuatable member such as a knob 52 is also drivingly connected to the shaft 54. When the knob 52 is used to actuate the orthosis manually, the motor 166 freewheels. Thus, the orthosis illustrated in FIG. 9 can be used either manually, or with an electric motor drive, or both. Therefore, the orthosis is ideally suited for both stretching therapy and CPM therapy.

Figure 8:
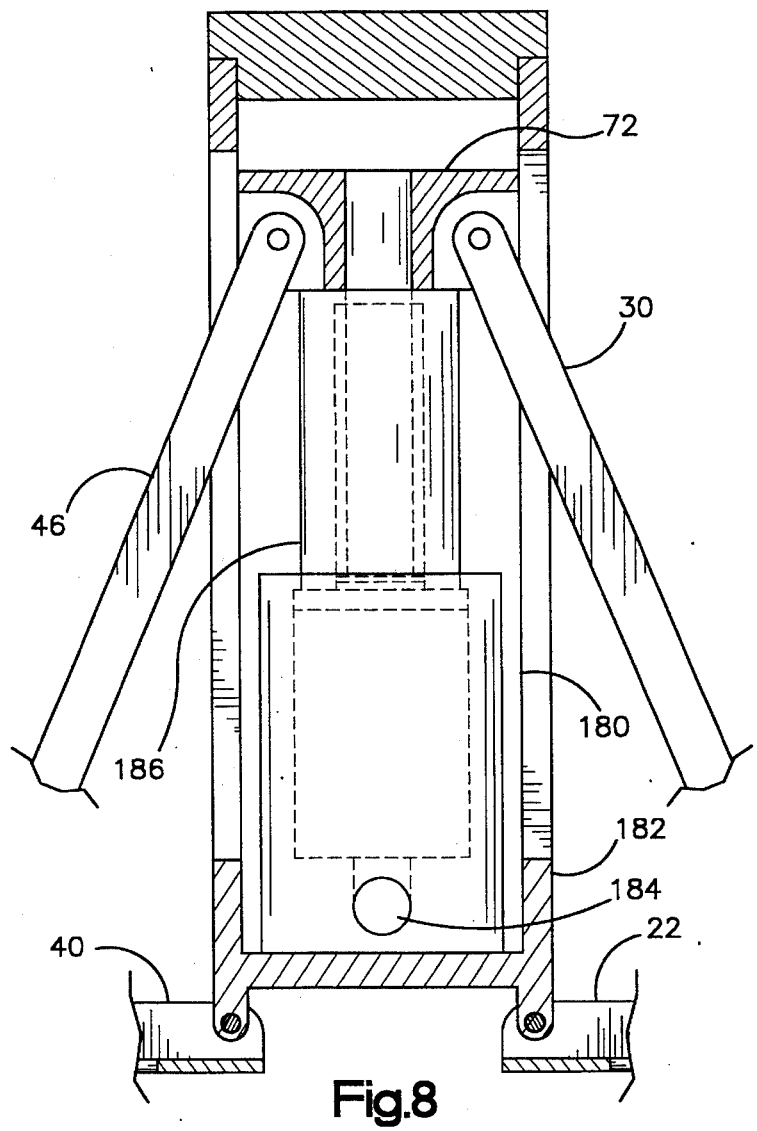
FIG. 8 is a view of an orthosis having a fluid drive.

Another type of power source, other than an electric motor, can also be used. For example, FIG. 8 illustrates the use of a hydraulic or pneumatic motor 180 as the drive mechanism for an orthosis in accordance with the present invention. The motor 180 is fixed in the lower portion of a tower 182. Fluid under pressure is supplied to the motor through a port 184. Actuation of the motor 180 causes a piston 186 to move axially in the tower 182. The piston 186 is connected to the arm actuator block 72. Axial movement of the piston 186 causes axial movement of the arm actuator block 72 to drive the lever arms 30 and 46 and the cuff arms 22 and 40 in the same manner as in the embodiment of FIGS. 1–5. Thus, it can be seen that many different types of power sources are suitable for use with an orthosis in accordance with the present invention.

An orthosis in accordance with the present invention can also be used to move a joint when one or both of the bone portions around the joint has projecting pins or K-wires. For example, after some types of bone surgery, the surgeon leaves pins or K-wires projecting from the bone through the skin. The fact that the arm is in this condition does not mean that therapy can not be applied. Rather, the pins or K-wires can be utilized to apply, directly to the bone, the force supplied by the orthosis.

The orthosis 190 illustrated in FIGS. 10–12 is one example. It should be understood that the design of such an orthosis can vary depending on the placement of the pins or k-wires and the therapy to be applied. The design will also vary depending on what particular joint is being moved by the orthosis.

In FIG. 10, the orthosis cuffs 192 each have longitudinally extending slots 196 for receiving cuff attachment screws 198. Each screw has an opening 200 for receiving a pin or K-wire 202. The screw 198 clamps onto the K-wire strongly enough to transmit torque to the bone through the pin or K-wire. As the cuffs slide along the cuff arms 204, and as the arms 204 pivot relative to the tower 205, the body portions to which the cuffs 192 are attached also are moved. Thus, the force of the orthosis is applied directly to bone through the pins or K-wires.

The opening 200 may be eccentrically located in the screw 198 as seen best in FIG. 12. Rotation of the screw 198 relative to the cuff 192 moves the pin 200 relative to the cuff 192. The cuff 192 can then be fixed in a given angular orientation relative to the body portion from which the pin 200 projects. This adjustment can be used to compensate for the particular location of the pins or K-wires, or can be used to apply an initial biasing force in one direction, or to position the limb portion initially within the cuff.

The cuff 192 may include, as best seen in FIG. 11, two cuff side portions 206 and 207 which are slidable relative to each other to position the cuff 192 as well as possible relative to the limb portion. A locking adjuster 208, which may be of a known construction to allow sliding movement then locking in position, is used to position the cuff side portions 206 and 207 relative to each other.

Further, the initial longitudinal positioning of a screw 198 along the cuff 192 can be adjusted using the positioner mechanism 209 shown in FIG. 10. The cuff attachment screw 198 is connected to a screw 210 which extends through a block 212 fixed to the cuff 192. The screw 210 is rotatable by an adjuster 214. Rotation of the screw 210 moves the cuff attachment screw 198 axially relative to the cuff 192. Again, this adjustment can be used to compensate for the particular location of the pins or K-wires, or can be used to apply an initial biasing force in one direction, or to position the limb portion initially within the cuff. It should be noted that this type of positioner mechanism, as well as the two-part cuff illustrated in FIG. 11, can be used in conjunction with orthoses other than the orthosis illustrated in FIGS. 10–12. It should also be noted that, if threaded pins are used in the bone, as is sometimes done, the pins can be threaded directly into nuts on the orthosis.

Another advantage of the gear drive mechanism is that it can provide an automatic locking mechanism for blocking movement of the parts of the orthosis in an undesired direction. Because the mechanism is geared down substantially to provide a mechanical advantage, it is difficult to rotate the gears by moving the cuff arms relative to each other. Therefore, if force is applied to the orthosis to extend a joint slightly against the resistance of the soft tissues of the joint, then the force is released, the orthosis and joint will maintain that extended position, and will not revert to the starting position.

This "locking" ability can also be provided by means of a ratchet drive mechanism. Such a mechanism is indicated schematically in FIG. 14, which shows a ratchet drive mechanism 230 of a known construction disposed in the line of force transmission between the knob 52 and the shaft 54 carrying gear 56. The ratchet drive mechanism 230 is operative to allow rotation of the knob 52 and the shaft 54 in one selected direction of rotation, while blocking rotation of the knob 52 and the shaft 54 in the opposite direction. Thus, the patient can turn the knob 52 in the desired direction to move the joint to which the orthosis is attached from a first position to a second position, then release the knob 52. The ratchet mechanism holds the knob 52 from turning back in the opposite direction, thus holding the joint in the second position.

These locking mechanisms are desirable, to maintain a joint in a selected position, because tissue is viscoelastic. That is, tissue will stretch a certain amount, then if it is maintained in that stretched condition for a period of time, will be able to stretch even more. This is the best way to establish or reestablish a range of motion in the soft tissues around a joint, as it does not involve damaging the tissue.

Accordingly, with an orthosis in accordance with the present invention, a patient can apply force to stretch tissue a desired amount by moving the orthosis from a first position to a second position. The patient can then stop applying force to the orthosis. The orthosis remains in the second position. The patient allows the tissue to remain in the stretched condition. The patient can then apply force to stretch tissue a further desired amount by moving the orthosis from the second position to a third position. This repeated stretching and resting of the tissue properly reestablishes a range of motion in the joint.

The orthosis may include means for monitoring, controlling, and/or limiting the mount of force applied by the orthosis, or the range of motion of the orthosis. This can be done in many different ways. A few illustrative methods are shown and described next.

Figure 14:
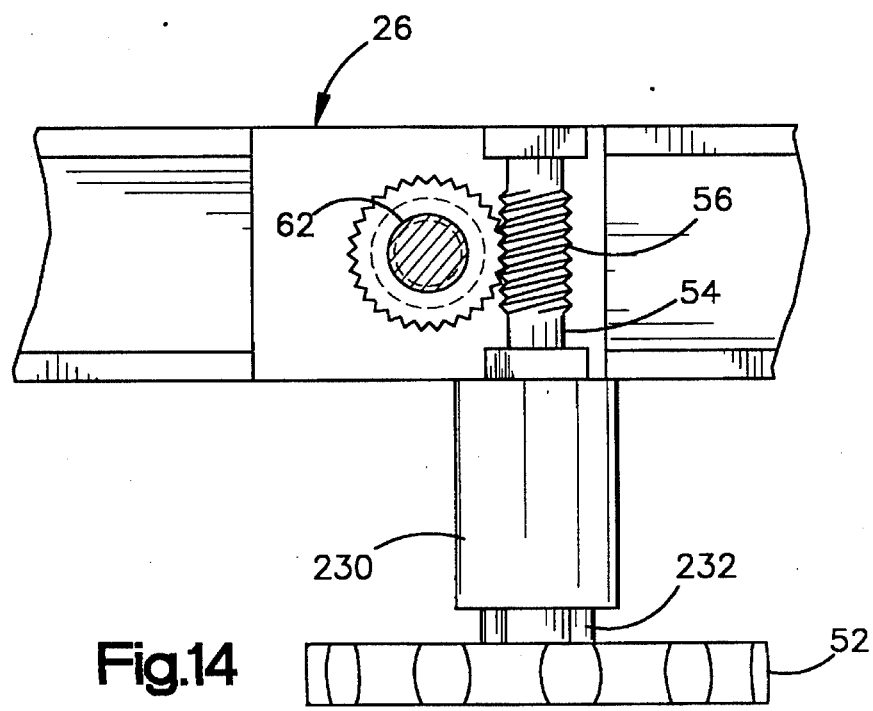
FIG. 14 is a view similar to FIG. 13 illustrating a ratchet drive in the drive mechanism.

One method is by providing wrench flats 232 as shown in FIG. 14 on the shaft 54 connected to the knob 52. A torque wrench can be applied to the wrench flats 232, and the shaft 54 can be turned with the torque wrench. Thus, the patient will know how much torque it takes to turn the shaft at any point during extension or flexion. This can be translated in various ways into an indication of how much force is being applied to the joint.

Another way of monitoring, controlling, and/or limiting the amount of force applied by the orthosis, when the orthosis includes an electric motor drive, involves measuring the work being performed by the electric motor. A torque sensor indicated schematically at 234 (FIG. 6), which may be of a known construction, measures the torque on the lead screw 154 of the drive mechanism. This value is indicative of the work being performed by the motor 150 and of the force applied to the joint. Alternatively, the microprocessor 160 may include circuitry of a known construction for measuring the current drawn by the electric motor 150. Again, this value is indicative of the work being performed by the motor 150 and thus of the force being applied to the joint.

Figure 13:
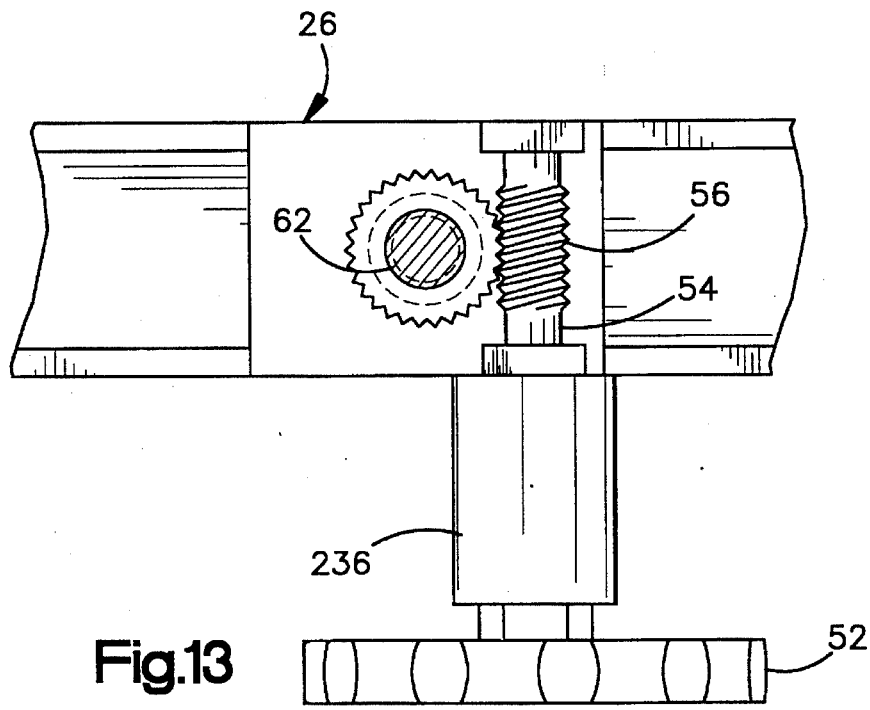
FIG. 13 is a view of a portion of an orthosis including a slip clutch in the drive mechanism.

To provide a positive limiting of the force applied to the joint, a slip clutch can be placed in the drive mechanism. For example, in FIG. 13 there is illustrated a slip clutch 236 of a known construction, in the line of force transmission between the knob 52 and the shaft 54. The slip clutch 236 blocks transmission of force above a certain amount. Thus, no matter how much the patient turns the knob 52, an excessive amount of force is not applied to the joint. The slip clutch 236 can be of the type which is settable to a given force value, and the orthosis may thus be individualized for each patient and/or each therapy session.

Another method of limiting force applied to the joint tissues is to provide phyical "stops" on the orthosis for limiting the range of motion of the orthosis and thus of the joint. There are many readily conceivable ways of doing this, and so they are not described in further detail herein.

In accordance with a further feature of the present invention, the drive mechanism for the cuff arms can be easily and quickly disengaged in case the patient wants to release force on the joint being moved.

An arm actuator block 240 (FIGS. 15–17) includes the openings 78 for the pins 76 which connect the lever arms to the arm actuator block 240. A slider 242 is slidably received in the arm actuator block 240. The slider 242 is fixed for axial movement with the arm actuator block 240. The slider 242 has two leg portions 244. Each leg portion has a cam slot 248. One or more ball members 250 is disposed between each leg portion and a lead screw 252, which preferably has a ball screw thread 254 formed thereon as best seen in FIG. 17. The ball members 250 are fixed for axial movement with the slider 242 and the arm actuator block 240.

A handle 256 including a push button 258 and a rod member 260 is fixed to and projects outwardly from the slider 242. The rod member 260 extends through a slot in the front plate (not shown) of the tower. The handle 256 is manually operable to move the slider 242 from a first position as shown in FIG. 15 to a second position as shown in FIG. 16.

When the slider 242 is in the first position as illustrated in FIG. 15, the ball members 250 are cammed radially inwardly into engagement with the ball screw thread 254 on the lead screw 252. Rotation of the lead screw 252 causes axial movement of the ball members 250, and thus results in axial movement of the slider 242 and of the arm actuator block 240. Axial movement of the arm actuator block 240, as described above, causes relative movement of the orthosis arms.

When the slider 242 is in the second position as shown in FIG. 16, the ball members 250 are cammed radially outwardly, by the ball screw thread 254, into the cam slots 248 in the slider leg portions 244. In this position, the ball members 250 are disengaged from the ball screw thread 254 of the lead screw 252. Rotation of the lead screw 252 does not result in axial movement of the ball members 250, the slider 242, or the arm actuator block 240.

Thus, there is provided an effective apparatus for disengaging the drive mechanism of an orthosis in accordance with the present invention. It is to be understood that other suitable mechanisms can be provided and are within the scope of the invention.

A gear drive mechanism for an orthosis of the present invention may include variable ratio gearing. For example, the lead screw 252 illustrated in FIG. 17 may be replaced with a lead screw 262 as illustrated in FIG. 18 which has a variable pitch. The gear teeth represented at 264 are closer together at the axial ends of the lead screw 262 than in the middle. The pitch 266 between adjacent teeth at the ends of the lead screw 262 is less than the pitch 268 between adjacent teeth at the center of the lead screw 262. Thus, an arm actuator block engaging the lead screw 262 will gain less axial motion at the extremes of motion, per revolution of the lead screw, than in the middle of the range of motion.

As noted above, because of the mechanical advantage provided by the drive mechanism and by the tower, an orthosis constructed in accordance with the present invention is lightweight and easily usable by the patient alone. If the orthosis is used on an elbow joint, the patient can use the orthosis while seated upright, with his arm on a suitable rest such as on a table, for example. If the orthosis is used for CPM on a knee joint, that is, cycling between flexion and extension, the patient can use it while seated in a chair. Such use of the orthosis of the present invention is highly preferable to the typical knee therapy which requires that the patient be lying in bed.

Figure 19:
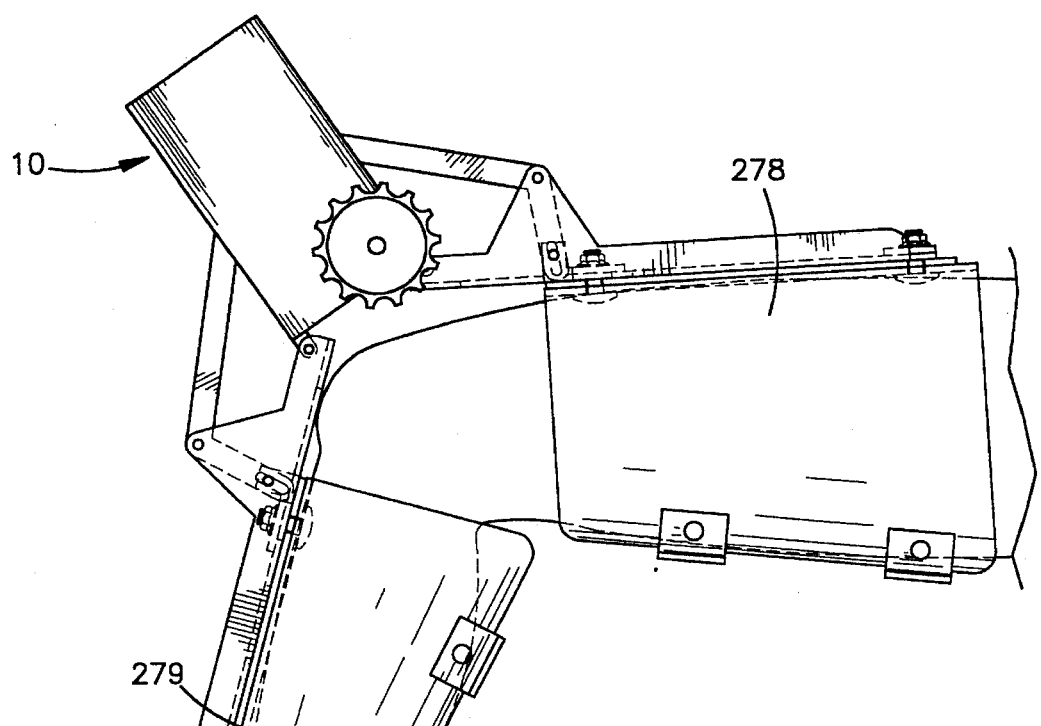
FIG. 19 is a view of an orthosis being used in combination with a rollable foot rest for knee therapy.
Figure 20:
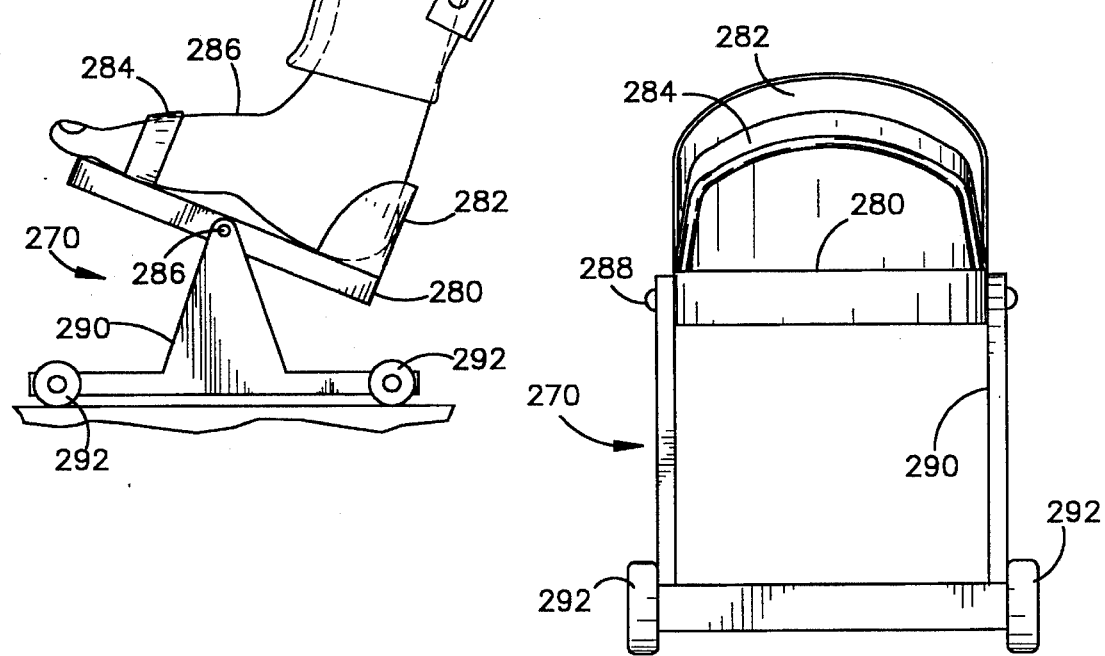
FIG. 20 is an end view of the foot rest of FIG. 19.

When the orthosis is used on a knee with a seated patient, it is deskable to provide, under the patient's foot, a device such as the foot support 270 illustrated in FIGS. 19–20. FIG. 19 illustrates an orthosis 10 as illustrated in FIGS. 1–5. The orthosis 10 is in position to flex and extend a knee joint 272. The knee joint is located between an upper leg 274 and a lower leg 276. A cuff 278 is attached to the upper leg 274. A cuff 279 is attached to the lower leg 276.

The foot support 270 includes a footrest 280. A heel cup 282 is fixed on the foot rest 280. An adjustable strap 284 secures the patient's foot 286 on the foot rest 280. The foot rest 280 is pivotally mounted at 268 to a frame 290. A plurality of rollers 292 are attached to the frame 290. The rollers 292 are rollable on the floor (not shown) underneath the patient. The foot support 270 allows the patient's foot 286 to move back and forth along the floor with minimal resistance. This permits the orthosis 10 to flex and extend the knee joint 272 easily. Thus, the patient can conveniently use the orthosis 10 on his knee joint while in any position such as a comfortable seated position, as compared to the difficulty and inconvenience of therapy while lying in a bed. Of course, the present orthosis can also be used while the patient is lying in bed.

It should also be noted that the orthoses of the present invention are suitable to hyperextend a joint, so that a slight overcorrection may be obtained if needed. Preferably, the orthosis is constructed so that the joint may be hyperextended by 5° to 7°. This provides the fullest range of motion desired. This can be accomplished by construction of the pivotal connection between the tower and the cuff arms to allow for such hyperextension.

The lever arms of the various orthoses illustrated are rigid members made of, for example, a metal such as aluminum or stainless steel so as to be able to transmit the necessary forces. It should be understood that any material of sufficient rigidity can be used, including a polymeric or composite material.

It is apparent that the orthosis of the present invention can apply much greater forces, safely through any range of motion, as compared to a spring-driven orthosis such as in the prior art. It is further apparent that the orthosis of the present invention attempts to limit compression of a joint through the joint's entire range of motion.

Further, it can be seen that the orthosis of the present invention is usable with the patient seated or in a lying position as opposed to a prior art device which can be used solely while lying in bed, and is thus more comfortable. The orthosis is light weight and portable, because of the mechanical advantage of the drive mechanism and the small power source needed. The orthosis provides both a manual stretching device and an electric CPM device with a manual override. The orthosis can be used to stretch tissue to increase range of motion, or to cycle through the range of motion to maintain it, or both. The orthosis can, when properly dimensioned, be used on any joint. It can also be used for motion other than flexion and extension, such as rotation, pronation, supination, etc., when suitably modified while incorporating the same operating principles.

From the above description of the invention, those skilled in the art will perceive improvements, changes and modifications in the invention. Such improvements, changes and modifications within the skill of the art are intended to be covered by the appended claims.

We claim:

1. A method of effecting relative movement between first and second body portions interconnected by a joint, said method comprising the steps of connecting a first cuff and a first cuff arm with the first body portion, connecting a second cuff and a second cuff arm with the second body portion, bending the joint by transmitting force through the first and second cuffs to the first and second body portions, and moving the first cuff along the first cuff arm during bending of the joint.

2. A method as set forth in claim 1 wherein said step of connecting a first cuff and a first cuff arm with the first body portion includes engaging an outer side surface of the first body portion with an inner side surface of the first cuff, said method further including gripping the first body portion with the first cuff with sufficient force to prevent relative movement between the outer side surface of the first body portion and the inner side surface of the first cuff during performance of said step of moving the first cuff along the first cuff arm.

3. A method as set forth in claim 1 wherein said step of connecting a first cuff and a first cuff arm with the first body portion includes connecting the first cuff arm with the first body portion with a first end portion of the first cuff arm adjacent to the joint, said step of connecting a second cuff and a second cuff arm with the second body portion includes connecting the second cuff arm with the second body portion with a first end portion of the second cuff arm adjacent to the joint and spaced from the first end portion of the first cuff arm and with a base link extending between the first end portions of the first and second cuff arms, said step of bending the joint includes pivoting the first cuff arm about a pivot connection between the base link and the first end portion of the first cuff arm and pivoting the second cuff arm about a pivot connection between the base link and the first end portion of the second cuff arm, the pivot connections between the first and second cuff arms and the base link being spaced apart on the base link.

4. A method as set forth in claim 1 wherein the joint and the first and second body portions define on one side of the joint an inner sector which decreases in angle as the joint is flexed and define on the opposite side of the joint an outer sector which decreases in angle as the joint is extended, said step of bending the joint includes transmitting force from a location in the outer sector to the first and second cuff arms, said step of moving the first cuff along the first cuff arm includes transmitting force from the location in the outer sector to the first cuff.

5. A method as set forth in claim 1 wherein the joint and the first and second body portions define on one side of the joint an inner sector which decreases in angle as the joint is flexed and define on the opposite side of the joint an outer sector which decreases in angle as the joint is extended, said step of bending the joint includes pivoting the first cuff arm about a first pivot connection which is disposed in the outer sector and pivoting the second cuff arm about a second pivot connection which is disposed in the outer sector and is spaced from the first pivot connection.

6. A method as set forth in claim 5 wherein said step of connecting the first cuff and the first cuff arm with the first body portion includes connecting the first cuff arm with the first body portion with the first cuff arm disposed in the outer sector, said step of connecting the second cuff and the second cuff arm with the second body portion includes connecting the second cuff arm with the second body portion with the second cuff arm disposed in the outer sector.

7. A method as set forth in claim 2 wherein said step of bending the Joint includes pivoting the first cuff arm about an axis which is offset from a central portion of the joint.

8. A method as set forth in claim 1 wherein said step of bending the joint includes bending the joint in extension, said step of moving the first cuff along the first cuff arm includes moving the first cuff along the first cuff arm in a direction toward the joint.

9. A method as set forth in claim 8 wherein said step of bending the joint in extension includes subjecting the joint to a limited amount of distraction.

10. A method as set forth in claim 1 wherein said step of bending the joint includes bending the joint in flexion, said step of moving the first cuff along the first cuff arm includes moving the first cuff along the first cuff arm in a direction away from the joint.

11. A method as set forth in claim 10 wherein said step of bending the joint in flexion includes subjecting the joint to a limited amount of distraction.

12. A method as set forth in claim 1 further including the step of providing an indication of the degree of flexion of the joint during performance of said step of bending the joint.

13. A method as set forth in claim 1 further including the step of adjusting an angle between one of the cuff arms and the one of the cuffs attached thereto by rotating the one cuff attached to the one cuff arm about a connection between the one cuff and the one cuff arm.

14. A method as set forth in claim 1 further including the steps of manually moving a member to effect the transmittal of force from the member through a mechanism to the first and second cuff arms, said step of bending the joint by transmitting force through the first and second cuffs to the first and second body portions includes transmitting force transmitted through the mechanism to the first and second cuff arms and from the first and second cuff arms to the first and second cuffs.

15. A method as set forth in claim 1 wherein said step of manually moving a member is performed by a person having the first and second body portions with which the first and second cuffs are connected.

16. A method as set forth in claim 1 further including the step of operating an electric motor to effect the transmittal of force from the electric motor through a mechanism to the first and second cuff arms, said step of bending the joint by transmitting force through the first and second cuffs to the first and second body portions includes transmitting the force transmitted through the mechanism to the first and second cuff arms to the first and second cuffs.

17. A method as set forth in claim 1 wherein said step of bending the joint includes providing relative movement between the first and second cuffs to bend the joint in one direction, allowing body tissue to stretch by retaining the cuffs against movement relative to each other after having performed said step of providing relative movement between the first and second cuffs, and, thereafter, providing additional relative movement between the first and second cuffs to further bend the joint in the one direction.

18. A method as set forth in claim 1 wherein said step of bending the joint includes bending the joint to one end of the joint's range of motion, holding the joint against movement from the one end of the joint's range of motion for a period of time, and then bending the joint to an end of the joint's range of motion opposite to the one end.

19. A method as set forth in claim 1 further including the step of operating a fluid motor to effect the transmittal of force from the fluid motor through a mechanism to the first and second cuff arms, said step of bending the joint by transmitting force through the first and second cuffs to the first and second body portions includes transmitting the force transmitted through the mechanism to the first and second cuff arms to the first and second cuffs.

20. A method as set forth in claim 1 wherein said steps of connecting a first cuff with the first body portion and connecting the second cuff with the second body portion includes connecting at least one of the cuffs with a pin which projects from a bone in one of the body portions, said step of bending the joint by transmitting force through the first and second cuffs to the first and second body portions includes transmitting force from the one cuff to the pin and transmitting force from the pin to the bone in the one of the body portions.

21. A method as set forth in claim 1 wherein said step of bending the joint by transmitting force through the first and second cuffs includes transmitting force through a mechanism by operating the mechanism in a first direction to bend the joint, said method further including retaining the joint in a condition to which it is bent with resistance provided by the mechanism to operation in a direction opposite to the first direction by force transmitted from the first and second body portions to the mechanism.

22. A method as set forth in claim 1 wherein said step of bending the joint by transmitting force through the first and second cuffs includes actuating a ratchet drive mechanism in a first direction and retaining the first and second cuffs against relative movement with the ratchet drive mechanism upon interruption of said step of actuating the ratchet drive mechanism.

23. A method as set forth in claim 22 wherein said step of actuating a ratchet drive mechanism is performed by a person having the first and second body portions with which the first and second cuffs are connected.

24. A method as set forth in claim 1 wherein said step of bending the joint includes effecting relative movement between the first and second cuffs in a first direction from a first position relative to each other to a second position relative to each other, interrupting said step of bending the joint for a period of time, and, thereafter, resuming said step of bending the joint by effecting relative movement between the first and second cuffs in the first direction from the second position relative to each other to a third position relative to each other.

25. A method as set forth in claim 1 wherein said step of bending the joint by transmitting force through the first and second cuffs to the first and second body portions includes applying force to a mechanism connected with the first and second cuffs and limiting the force applied to the mechanism to a predetermined maximum force.

26. A method as set forth in claim 25 wherein said step of applying force to a mechanism includes applying torque to the mechanism, said step of limiting the force applied to the mechanism includes limiting the torque applied to the mechanism.

27. A method as set forth in claim 25 wherein said step of applying force to the mechanism includes operating an electric motor to drive the mechanism, said step of limiting the force applied to the mechanism includes limiting the force applied to the mechanism by the electric motor during operation of the electric motor.

28. A method as set forth in claim 25 wherein said step of applying force to a mechanism is performed by a person having the first and second body portions with which the first and second cuffs are connected and includes manually applying force to an input to the mechanism, said step of limiting the force applied to the mechanism includes limiting the force transmitted between the input to the mechanism and the mechanism.

29. A method as set forth in claim 1 further including the step of moving the second cuff along the second cuff arm simultaneously with movement of the first cuff along the first cuff arm during bending of the joint.

30. A method as set forth in claim 29 wherein said steps of moving the first and second cuffs along the first and second cuff arms includes moving the first cuff along the first cuff arm in a direction toward the joint and moving the second cuff along the second cuff arm in a direction toward the joint simultaneously with movement of the first cuff along the first cuff arm in a direction toward the joint.

31. A method as set forth in claim 30 wherein said steps of moving the first and second cuffs along the first and second cuff arms includes moving the first cuff along the first cuff arm in a direction away from the joint and moving the second cuff along the second cuff arm in a direction away from the joint simultaneously with movement of the first cuff along the first cuff arm in a direction away from the joint.

32. A method as set forth in claim 1 further including the step of manually actuating a linkage to transmit force to effect relative movement between the first and second cuff arms and to simultaneously therewith effect movement of first cuff along the first cuff arm.

33. A method as set forth in claim 32 wherein said step of manually actuating a linkage is performed by a person having the first and second body portions with which the first and second cuffs are connected.

34. A method as set forth in claim 33 wherein said step of manually actuating a linkage to transmit force to effect relative movement between the first and second cuff arms includes manually actuating the linkage in a first direction to effect relative movement between the first and second cuff arms to first positions relative to each other, maintaining the first and second cuff arms stationary in the first positions relative to each other for a predetermined length of time, and, thereafter, manually actuating the linkage in the first direction to again effect relative movement between the first and second cuff arms.

35. A method as set forth in claim 1 wherein said step of bending the joint by transmitting force through first and second cuffs to the first and second body portions includes moving an actuator member along a path, transmitting force from the actuator member through a first link to the first cuff arm to pivot the first cuff arm in a first direction about a pivot connection between the first cuff arm and a base link as the actuator member moves along the path, and transmitting force from the actuator member through a second link to the second cuff arm to pivot the second cuff arm in a second direction about a pivot connection between the second cuff arm and the base link as the actuator member moves along the path, said step of moving the first cuff along the first cuff arm during bending of the joint includes moving the first cuff along the first cuff arm under the influence of force transmitted from the actuator member through the first link to the first cuff as the actuator member moves along the path.

36. A method as set forth in claim 35 wherein said step of moving the actuator member along a path includes moving the actuator member along a path which extends through the joint.

37. A method as set forth in claim 35 wherein said step of moving the actuator member along a path includes effecting relative rotation between internally and externally threaded members to move one of the threaded members connected with the actuator member relative to the other threaded member.

38. A method as set forth in claim 35 further including the step of moving the second cuff along the second cuff arm during bending of the joint, said step of moving the second cuff along the second cuff arm during bending of the joint includes moving the second cuff along the second cuff arm under the influence of force transmitted from the actuator member through the second link to the second cuff as the actuator member moves along the path.

39. A method of effecting relative movement between first and second body portions interconnected by a joint, said method comprising the steps of connecting a first cuff and a first cuff arm with the first body portion, connecting a second cuff and a second cuff arm with the second body portion with the first and second cuff arms interconnected by a base link, moving an actuator member along a path extending transverse to the base link, transmitting force from the actuator member through a first link to the first cuff arm to pivot the first cuff arm in a first direction of rotation about a pivot connection between the first cuff arm and the base link as the actuator member moves along the path, transmitting force from the actuator member through a second link to the second cuff arm to pivot the second cuff arm in a second direction of rotation about a pivot connection between the second cuff arm and the base link as the actuator member moves along the path, the second direction of rotation being opposite from the first direction of rotation, transmitting force from the first and second cuff arms to the first and second cuffs as the actuator member moves along the path, and bending the joint under the influence of the force transmitted from the first and second cuff arms to the first and second cuffs as the actuator member moves along the path.

40. A method as set forth in claim 39 further including the step of transmitting force from the first link to the first cuff to move the first cuff along the first cuff arm as the actuator member moves along the path.

41. A method as set forth in claim 40 further including the step of transmitting force from the second link to the second cuff to move the second cuff along the second cuff arm as the actuator member moves along the path.

42. A method as set forth in claim 39 wherein said step of moving an actuator member along a path extending transverse to the base link includes moving the actuator member along a linear path which extends through the base link.

43. A method as set forth in claim 39 wherein said step of transmitting force from the actuator member through a first link to the first cuff arm to pivot the first cuff arm in a first direction of rotation includes pivoting the first link about a pivot connection between the first link and the actuator member and pivoting the first link about a pivot connection between the first link and the first cuff arm, said step of transmitting force from the actuator member through a second link to the second cuff arm to pivot the second cuff arm in a second direction of rotation includes pivoting the second link about a pivot connection between the second link and the actuator member and pivoting the second link about a pivot connection between the second link and the second cuff arm.

44. A method as set forth in claim 39 wherein said step of transmitting force from the actuator member through a first link to the first cuff arm to pivot the first cuff arm in a first direction of rotation includes pivoting the first link about a pivot connection between a portion of the first link and the actuator member and pivoting the first link about a pivot connection between the first cuff arm and a portion of the first link, said step of transmitting force from the actuator member through a second link to the second cuff arm to pivot the second cuff arm in a second direction of rotation includes pivoting the second link about a pivot connection between a portion of the second link and the actuator member and pivoting the second link about a pivot connection between the second cuff arm and a portion of the second link, said method further including the steps of moving the first cuff along the first cuff arm under the influence of force transmitted from the first link to the first cuff during pivoting of the first link about the pivot connection between the first cuff arm and the first link, and moving the second cuff along the second cuff arm under the influence of force transmitted from the second link to the second cuff during pivoting of the second link about the pivot connection between the second cuff arm and the second link.

45. A method as set forth in claim 44 wherein said step of moving an actuator member along a path extending transverse to the base link includes moving the actuator member toward the base link, said step of moving the first cuff along the first cuff arm includes moving the first cuff along the first cuff arm in a direction away from the base link, said step of moving the second cuff along the second cuff arm includes moving the second cuff along the second cuff arm in a direction away from the base link.

46. A method as set forth in claim 44 wherein said step of moving an actuator along a path extending transverse to the base link includes moving the actuator member away from the base link, said step of moving the first cuff along the first cuff arm includes moving the first cuff along the first cuff arm in a direction toward the base link, said step of moving the second cuff along the second cuff arm includes moving the second cuff along the second cuff arm in direction toward the base link.

47. A method as set forth in claim 39 wherein said step of moving an actuator member along a path transverse to the base link includes providing relative rotation between internally and externally threaded members.

48. A method as set forth in claim 39 wherein said step of moving an actuator member along a path transverse to the base link includes manually applying force to an input member to effect movement of the actuator member along the path under the influence of force transmitted from the input member.

49. A method as set forth in claim 39 further including the step of supporting a motor on the base link, said step of moving an actuator member along a path transverse to the base link includes transmitting force from the motor to the actuator member.

50. A method as set forth in claim 39 wherein said step of transmitting force from the actuator member through the first link to the first cuff arm to pivot the first cuff arm in a first direction of rotation about a pivot connection between the first cuff arm and the base link includes pivoting the first cuff arm about a first axis which is offset from a central portion of the joint, the step of transmitting force from the actuator member through a second link to the second cuff arm to pivot the second cuff arm in a second direction about a pivot connection between the second cuff arm and the base link includes pivoting the second cuff arm about a second axis which is offset from a central portion of the joint and is offset from the first axis.

51. A method as set forth in claim 39 further including providing an indication of the angular relationship between the first and second cuff arms during performance of said steps of transmitting force from the actuator member through the first link to the first cuff arm to pivot the first cuff arm in a first direction of rotation and transmitting force from the actuator member through the second link to the second cuff arm to pivot the second cuff arm in a second direction of rotation.

52. A method as set forth in claim 39 further including the step of adjusting the position of the first cuff relative to the first cuff arm by pivoting the first cuff about an axis which extends through the first cuff arm in a direction transverse to an axis about which the first cuff arm pivots about the pivot connection between the first cuff arm and the base link.

53. A method as set forth in claim 39 wherein said step of moving an actuator member along a path extending transverse to the base link includes manually moving an input member to effect the transmittal of force from the input member through a mechanism to the actuator member.

54. A method as set forth in claim 53 wherein said step of manually moving an input member is performed by a person having the first and second body portions with which the first and second cuffs are connected.

55. A method as set forth in claim 39 wherein said step of moving an actuator member along a path extending transversely to the base link includes moving the actuator member along the path in a first direction to a first position, retaining the actuator member in the first position for a length of time sufficient to allow body tissue to stretch, and, thereafter, moving the actuator member along the path in the first direction away from the first position.

56. A method as set forth in claim 39 wherein said step of connecting a first cuff and a first cuff arm with the first body portion includes connecting the first cuff with a pin which projects from a bone in the first body portion, said step of bending the joint includes transmitting force from the first cuff to the pin and transmitting force from the pin to the bone in the first body portion.

57. A method as set forth in claim 39 wherein said step of moving an actuator member along a path extending transverse to the base link includes applying force to a mechanism connected with the actuator member and limiting the force applied to the mechanism to a predetermined force.

58. A method as set forth in claim 39 wherein said step of connecting a first cuff and a first cuff arm with the first body portion includes engaging an outer side surface of the first body portion with an inner side surface of the first cuff, said step of connecting a second cuff and a second cuff arm with the second body portion includes engaging an outer side surface of the second body portion with an inner side surface of the second cuff, said method further including moving the first cuff along the first cuff arm while bending the joint and while gripping the first body portion with the first cuff with sufficient force to prevent movement between the outer side surface of the first body portion and the inner side surface of the first cuff during movement of the first cuff along the first cuff arm, and moving the second cuff along the second cuff arm while bending the joint and while gripping the second body portion with the second cuff with sufficient force to prevent movement between the outer side surface of the second body portion and the inner side surface of the second cuff during movement of the second cuff along the second cuff arm.

59. A method as set forth in claim 39 wherein said step of connecting a first cuff and a first cuff arm with the first body portion includes connecting the first cuff arm with the first body portion with a first end portion of the first cuff arm adjacent to the joint, said step of connecting a second cuff and a second cuff arm with the second body portion includes connecting the second cuff arm with the second body portion with a first end portion of the second cuff arm adjacent to the joint and spaced from the first end portion of the first cuff arm.

60. A method as set forth in claim 39 wherein the joint and the first and second body portions define on one side of the joint an inner sector which decreases in angle as the joint is flexed and define on the opposite side of the joint an outer sector which decreases in angle as the joint is extended, said step of moving the actuator member along a path extending transverse to the base link includes moving the actuator member along a portion of the path disposed in the outer sector.

61. A method as set forth in claim 60 wherein said step of transmitting force from the actuator member through a first link to the first cuff arm to pivot the first cuff arm in a first direction of rotation about a pivot connection between the first cuff arm and the base link includes pivoting the first cuff arm about a pivot connection which is disposed in the outer sector, said step of transmitting force from the actuator member through a second link to the second cuff arm to pivot the second cuff arm in a second direction of rotation about a pivot connection between the second cuff arm and the base link includes pivoting the second cuff arm about a pivot connection which is disposed in the outer sector.

62. A method of effecting relative movement between first and second body portions interconnected by a joint, said method comprising the steps of connecting a first cuff and a first cuff arm with the first body portion, connecting a second cuff and a second cuff arm with the second body portion, thereafter, moving an actuator member relative to the first and second cuff arms, pivoting the first cuff arm under the influence of force transmitted from the actuator member through a first link connected with the actuator member and first cuff arm during movement of the actuator member, moving the first cuff along the first cuff arm under the influence of force transmitted from the actuator member during movement of the actuator member, pivoting the second cuff arm under the influence of force transmitted from the actuator member through a second link connected with the actuator member and second cuff arm during movement of the actuator member, and moving the second cuff along the second cuff arm under the influence of force transmitted from the actuator member during movement of the actuator member.

63. A method as set forth in claim 62 wherein said step of moving the first cuff along the first cuff arm is performed simultaneously with performance of said step of moving the second cuff along the second cuff arm.

64. A method as set forth in claim 62 wherein said step of moving an actuator member relative to the first and second cuff arms includes pivoting the first and second links under the influence of force transmitted to portions of the first and second links from the actuator member, said step of moving the first cuff along the first cuff arm includes moving the first cuff under the influence of force transmitted to the first cuff from a portion of the first link during pivotal movement of the first link under the influence of force transmitted to a portion of the first link from the actuator member, said step of moving the second cuff along the second cuff arm includes moving the second cuff under the influence of force transmitted to the second cuff from a portion of the second link during pivotal movement of the second link under the influence of force transmitted to a portion of the second link from the actuator member.

65. A method as set forth in claim 62 wherein said step of pivoting the first cuff arm includes pivoting the first cuff arm in a first direction about an axis which is offset from a central portion of the joint and said step of pivoting the second cuff arm includes pivoting the second cuff arm in a second direction which is opposite to the first direction about an axis which is offset from the central portion of the joint.

66. A method as set forth in claim 62 wherein said step of moving the first cuff along the first cuff arm includes moving the first cuff along the first cuff arm in a direction toward the joint, said step of moving the second cuff along the second cuff arm includes moving the second cuff along the second cuff arm in a direction toward the joint during movement of the first cuff along the first cuff arm in a direction toward the joint.

67. A method as set forth in claim 62 wherein said step of moving the first cuff along the first cuff arm includes moving the first cuff along the first cuff arm in a direction away from the joint, said step of moving the second cuff along the second cuff arm includes moving the second cuff along the second cuff arm in a direction away from the joint during movement of the first cuff along the first cuff arm in a direction away from the joint.

68. A method as set forth in claim 62 further including the step of bending the joint under the influence of force transmitted from the first cuff to the first body portion during pivoting of the first cuff arm and under the influence of force transmitted from the second cuff to the second body portion during pivoting of the second cuff arm.

69. A method as set forth in claim 68 wherein said step of bending the joint includes bending the joint in extension, said step of moving the first cuff along the first cuff arm includes moving the first cuff along the first cuff arm in a direction toward the joint during bending of the joint, said step of moving the second cuff along the second cuff arm includes moving the second cuff along the second cuff arm in a direction toward the joint during bending of the joint.

70. A method as set forth in claim 69 wherein said step of bending the joint in extension includes subjecting the joint to a limited amount of distraction.

71. A method as set forth in claim 68 wherein said step of bending the joint includes bending the joint in flexion, said step of moving the first cuff along the first cuff arm includes moving the first cuff along the first cuff arm in a direction away from the joint during bending of the joint, said step of moving the second cuff along the second cuff arm includes moving the second cuff along the second cuff arm in a direction away from the joint during bending of the joint.

72. A method as set forth in claim 71 wherein said step of bending the joint in flexion includes subjecting the joint to a limited amount of distraction.

73. A method as set forth in claim 68 further including the step of providing an indication of the degree of flexion of the joint during performance of said step of bending the joint.

74. A method as set forth in claim 68 wherein said step of bending the joint includes pivoting the first cuff arm in a first direction and pivoting the second cuff arm in a second direction which is opposite to the first direction, allowing body tissue to stretch by retaining the first and second cuff arms against pivotal movement after having performed said steps of pivoting the first cuff arm in a first direction and pivoting the second cuff arm in a second direction, and, thereafter, pivoting the first cuff arm in the first direction and pivoting the second cuff arm in the second direction.

75. A method as set forth in claim 68 wherein said step of bending the joint includes bending the joint to one end of the joint's range of motion, holding the joint against movement from the one end of the joint's range of motion for a period of time, and then bending the joint to an end of the joint's range of motion opposite to the one end.

76. A method as set forth in claim 68 wherein said steps of moving an actuator member relative to the first and second cuff arms and bending the joint include operating a mechanism to move the actuator member in a first direction to bend the joint, said method further including retaining the joint in a condition to which it is bent by resisting movement of the actuator member in a direction opposite to the first direction with resistance provided by the mechanism.

77. A method as set forth in claim 68 wherein said step of moving the actuator member relative to the cuff arms includes moving the actuator member in a first direction from a first position to a second position, interrupting said step of moving the actuator member in a first direction for a period of time upon movement of the actuator member to the second position, and, thereafter, moving the actuator member in the first direction from the second position, said step of bending the joint includes bending the joint in one direction from a first condition to a second condition during movement of the actuator member in the first direction from the first position to the second position, interrupting said step of bending the joint during interruption of said step of moving the actuator member in the first direction, and, thereafter, bending the joint in the one direction from the second condition toward a third condition during movement of the actuator member in the first direction from the second position.

78. A method as set forth in claim 62 wherein said step of moving an actuator member relative to the first and second cuff arms includes manually moving an input member to effect the transmittal of force from the input member to the actuator member, said steps of pivoting the first and second cuff arms and moving the first and second cuff arms being performed under the influence of force transmitted from the input member to the actuator member.

79. A method as set forth in claim 78 wherein said step of manually moving the input member is performed by a person having the first and second body portions with which the first and second cuffs are connected.

80. A method as set forth in claim 62 wherein said step of moving an actuator member relative to the first and second cuff arms includes operating an electric motor to effect the transmittal of force from the electric motor to the actuator member.

81. A method as set forth in claim 62 wherein said step of moving an actuator member relative to the first and second cuff arms includes operating a fluid motor to effect the transmittal of force from the fluid motor to the actuator member.

82. A method as set forth in claim 62 wherein said step of moving an actuator member relative to the first and second cuff arms includes transmitting force through a mechanism by operating the mechanism in a first direction, said method further including retaining the actuator member and first and second links against movement with resistance provided by the mechanism to operation in a direction opposite to the first direction by force transmitted from the actuator member to the mechanism.

83. A method as set forth in claim 62 wherein said step of moving an actuator member relative to the first and second cuff arms includes applying force to a mechanism connected with the actuator member and limiting the force applied to the mechanism to a predetermined maximum force.

84. A method as set forth in claim 83 wherein said step of applying force to a mechanism includes applying torque to the mechanism, said step of limiting the force applied to the mechanism includes limiting the torque applied to the mechanism.

85. A method as set forth in claim 83 wherein said step of applying force to a mechanism includes operating a motor to drive the mechanism, said step of limiting the force applied to the mechanism includes limiting the force applied to the mechanism by the motor during operation of the motor.

86. A method as set forth in claim 83 wherein said step of applying force to a mechanism is performed by a person having the first and second body portions with which the first and second cuffs are connected and includes manually applying force to an input to the mechanism, said step of limiting the force applied to the mechanism includes limiting the force transmitted between the input to the mechanism and the mechanism.

87. A method as set forth in claim 62 wherein said step of moving an actuator member relative to the first and second cuff arms includes effecting relative rotation between internally and externally threaded members to move one of the threaded members and the actuator member relative to the other threaded member.

88. A method as set forth in claim 62 wherein said step of connecting a first cuff and a first cuff arm with the first body portion includes engaging an outer side surface of the first body portion with an inner side surface of the first cuff, said step of connecting a second cuff and a second cuff arm with the second body portion includes engaging an outer side surface of the second body portion with an inner side surface of the second cuff, said method further including gripping the first body portion with the first cuff with sufficient force to prevent movement between the outer side surface of the first body portion and the inner side surface of the first cuff during movement of the first cuff along the first cuff arm, and gripping the second body portion with the second cuff with sufficient force to prevent movement between the outer side surface of the second body portion and the inner side surface of the second cuff during movement of the second cuff along the second cuff arm.

89. A method as set forth in claim 62 wherein said step of connecting a first cuff and a first cuff arm with the first body portion includes connecting the first cuff arm with the first body portion with a first end portion of the first cuff arm adjacent to the joint, said step of connecting a second cuff and a second cuff arm with the second body portion includes connecting the second cuff with the second body portion with a first end portion of the second cuff arm adjacent to the joint and spaced from the first end portion of the first cuff arm and with a base link extending between the first end portions of the first and second cuff arms, said step of pivoting the first cuff arm including pivoting the first cuff arm about a pivot connection between the base link and the first end portion of the first cuff arm, said step of pivoting the second cuff arm including pivoting the second cuff arm about a pivot connection between the base link and the first end portion of the second cuff arm.

90. A method as set forth in claim 62 wherein the joint and the first and second body portions define on one side of the joint an inner sector which decreases in angle as the joint is flexed and define on the opposite side of the joint an outer sector which decrease in angle as the joint is extended, said step of moving an actuator member relative to the first and second cuff arms includes moving the actuator member along a portion of a path which is disposed in the outer sector, said step of pivoting the first cuff arm under the influence of force transmitted from the actuator member through the first link being performed with at least a portion of the first link in the outer sector, said step of pivoting the second cuff arm under the influence of force transmitted from the actuator member through the second link being performed with at least a portion of the second link in the outer sector.

91. A method for effecting relative movement between first and second body portions interconnected by a joint, said method comprising the steps of connecting a first cuff and cuff arm with the first body portion, connecting a second cuff and cuff arm with the second body portion, bending the joint by transmitting force through the first and second cuffs to the first and second body portions, moving the first cuff along the first cuff arm during bending of the joint, and moving the second cuff along the second cuff arm during bending of the joint.

92. A method as set forth in claim 91 wherein said step of bending the joint, moving the first cuff along the first cuff arm and moving the second cuff along the second cuff arm include manually moving an input member, transmitting force from the input member to the first and second cuff arms to move the first and second cuff arms relative to each other, and transmitting force from the input member to the first and second cuffs to move the first and second cuffs along the first and second cuff arms.

93. A method as set forth in claim 92 wherein said step of manually moving an input member is performed by a person having the first and second body portions with which the first and second cuffs are connected.

94. A method as set forth in claim 93 further including the step of limiting the force transmitted to the first and second cuff arms from the input member to a predetermined maximum force.

95. A method as set forth in claim 91 further including the step of moving an actuator member relative to the first and second cuff arms, said step of bending the joint includes pivoting the first cuff arm under the influence of force transmitted through a first force transmitting member during movement of the actuator member and pivoting the second cuff arm under the influence of force transmitted through a second force transmitting member during movement of the actuator member, said step of moving the first cuff along the first cuff arm includes moving the first cuff along the first cuff arm under the influence of force transmitted from the actuator member through the first force transmitting member, said step of moving the second cuff along the second cuff arm includes moving the second cuff along the second cuff arm under the influence of force transmitted from the actuator member through the second force transmitting member.

96. A method as set forth in claim 91 wherein said step of bending the joint includes pivoting the first and second cuff arms about axes which are offset from a central portion of the joint.

97. A method as set forth in claim 91 wherein said step of bending the joint includes bending the joint in extension, said step of moving the first cuff along the first cuff arm includes moving the first cuff along the first cuff arm in a direction toward the joint, said step of moving the second cuff along the second cuff arm includes moving the second cuff along the second cuff arm in a direction toward the joint.

98. A method as set forth in claim 97 wherein said step of bending the joint in extension includes subjecting the joint to a limited amount of distraction.

99. A method as set forth in claim 91 wherein said step of bending the joint includes bending the joint in flexion, said step of moving the first cuff along the first cuff arm includes moving the first cuff along the first cuff arm in a direction away from the joint, said step of moving the second cuff along the second cuff arm includes moving the second cuff along the second cuff arm in a direction toward the joint.

100. A method as set forth in claim 99 wherein said step of bending the joint in flexion includes subjecting the joint to a limited amount of distraction.

101. A method as set forth in claim 91 further including the step of providing an indication of the degree of flexion of the joint during performance of said step of bending the joint.

102. A method as set forth in claim 91 further including the step of adjusting an angle between one of the cuff arms and the one of the cuffs attached thereto by rotating the one cuff attached to the one cuff arm about a connection between the one cuff and the one cuff arm.

103. A method as set forth in claim 91 further including the steps of manually moving a member to effect the transmittal of force from the member through a linkage to the first and second cuff arms, said step of bending the joint by transmitting force through the first and second cuffs to the first and second body portions includes transmitting force transmitted through the linkage to the first and second cuff arms and from the first and second cuff arms to the first and second cuffs, said step of moving the first cuff along the first cuff arm includes transmitting force from the member through the linkage to the first cuff, said step of moving the second cuff along the second cuff arm includes transmitting force from the member through the linkage to the second cuff.

104. A method as set forth in claim 103 wherein said step of manually moving a member is performed by a person having the first and second body portions with which the first and second cuffs are connected.

105. A method as set forth in claim 91 further including the step of operating a motor to effect the transmittal of force from the motor to the first and second cuff arms, said step of bending the joint by transmitting force through the first and second cuffs to the first and second body portions includes transmitting the force transmitted from the motor to the first and second cuff arms to the first and second cuffs, said step of moving the first cuff along the first cuff arm includes transmitting force from the motor to the first cuff, said step of moving the second cuff along the second cuff arm includes transmitting force from the motor to the second cuff.

106. A method as set forth in claim 91 Wherein said step of bending the joint includes providing relative movement between the first and second cuffs to bend the joint in one direction, allowing body tissue to stretch by retaining the cuffs against movement relative to each other after having performed said step of providing relative movement between the first and second cuffs, and, thereafter, providing additional relative movement between the first and second cuffs to further bend the joint in the one direction.

107. A method as set forth in claim 91 wherein said step of bending the joint includes bending the joint to one end of the joint's range of motion, holding the joint against movement from the one end of the joint's range of motion for a period of time, and then bending the joint to an end of the joint's range of motion opposite to the one end.

108. A method as set forth in claim 91 further including the step of operating a motor to effect the transmittal of force from the motor through first and second links to the first and second cuff arms, said step of moving the first cuff along the first cuff arm includes transmitting force from the motor to the first cuff through the first link, said step of moving the second cuff along the second cuff arm includes transmitting force from the motor to the second cuff through the second link.

109. A method as set forth in claim 91 wherein said steps of connecting a first cuff with the first body portion and connecting the second cuff with the second body portion includes connecting at least one of the cuffs with a pin which projects from a bone in one of the body portions, said step of bending the joint by transmitting force through the first and second cuffs to the first and second body portions includes transmitting force from the one cuff to the pin and transmitting force from the pin to the bone in the one of the body portions.

110. A method as set forth in claim 91 Wherein said step of bending the joint by transmitting force through the first and second cuffs includes transmitting force through a mechanism by operating the mechanism in a first direction to bend the joint, said method further including retaining the joint in a condition to which it is bent with resistance provided by the mechanism to operation in a direction opposite to the first direction by force transmitted from the first and second body portions to the mechanism.

111. A method as set forth in claim 91 wherein said step of bending the joint by transmitting force through the first and second cuffs includes actuating a ratchet drive mechanism in a first direction and retaining the first and second cuffs against relative movement with the ratchet drive mechanism upon interruption of said step of actuating the ratchet drive mechanism.

112. A method as set forth in claim 111 wherein said step of actuating a ratchet drive mechanism is performed by a person having the first and second body portions with which the first and second cuffs are connected.

113. A method as set forth in claim 91 wherein said step of bending the joint includes effecting relative movement between the first and second cuffs in a first direction from a first position relative to each other to a second position relative to each other, interrupting said step of bending the joint for a period of time, and, thereafter, resuming said step of bending the joint by effecting relative movement between the first and second cuffs in the first direction from the second position relative to each other to a third position relative to each other.

114. A method as set forth in claim 91 wherein said step of bending the joint by transmitting force through the first and second cuffs to the first and second body portions includes applying force to a mechanism connected with the first and second cuffs and limiting the force applied to the mechanism to a predetermined maximum force.

115. A method as set forth in claim 114 wherein said step of applying force to a mechanism includes applying torque to the mechanism, said step of limiting the force applied to the mechanism includes limiting the torque applied to the mechanism.

116. A method as set forth in claim 114 wherein said step of applying force to the mechanism includes operating an electric motor to drive the mechanism, said step of limiting the force applied to the mechanism includes limiting the force applied to the mechanism by the electric motor during operation of the electric motor.

117. A method as set forth in claim 114 wherein said step of applying force to a mechanism is performed by a person having the first and second body portions with which the first and second cuffs are connected and includes manually applying force to an input to the mechanism, said step of limiting the force applied to the mechanism includes limiting the force transmitted between the input to the mechanism and the mechanism.

118. A method as set forth in claim 91 wherein said steps of moving the first and second cuffs along the first and second cuff arms includes moving the first cuff along the first cuff arm in a direction toward the joint and moving the second cuff along the second cuff arm in a direction toward the joint simultaneously with movement of the first cuff along the first cuff arm in a direction toward the joint.

119. A method as set forth in claim 118 wherein said steps of moving the first and second cuffs along the first and second cuff arms includes moving the first cuff along the first cuff arm in a direction away from the joint and moving the second cuff along the second cuff arm in a direction away from the joint simultaneously with movement of the first cuff along the first cuff arm in a direction away from the joint.

120. A method as set forth in claim 91 further including the step of manually actuating a linkage to transmit force to effect relative movement between the first and second cuff arms and to simultaneously therewith effect movement of first cuff along the first cuff arm and movement of the second cuff along the second cuff arm.

121. A method as set forth in claim 120 wherein said step of manually actuating a linkage is performed by a person having the first and second body portions with which the first and second cuffs are connected.

122. A method as set forth in claim 120 wherein said step of manually actuating a linkage to transmit force to effect relative movement between the first and second cuff arms includes manually actuating the linkage in a first direction to effect relative movement between the first and second cuff arms to first positions relative to each other, maintaining the first and second cuff arms stationary in the first positions relative to each other for a predetermined length of time, and, thereafter, manually actuating the linkage in the first direction to again effect relative movement between the first and second cuff arms.

123. A method as set forth in claim 91 wherein said step of bending the joint by transmitting force through first and second cuffs to the first and second body portions includes moving an actuator member along a path, transmitting force from the actuator member through a first force transmitting member to the first cuff arm to pivot the first cuff arm in a first direction about a pivot connection between the first cuff arm and a base link as the actuator member moves along the path, and transmitting force from the actuator member through a second force transmitting member to the second cuff arm to pivot the second cuff arm in a second direction about a pivot connection between the second cuff arm and the base link as the actuator member moves along the path, said step of moving the first cuff along the first cuff arm during bending of the joint includes moving the first cuff along the first cuff arm under the influence of force transmitted from the actuator member through the first force transmitting member to the first cuff as the actuator member moves along the path, said step of moving the second cuff along the second cuff arm during bending of the joint includes moving the second cuff along the second cuff arm under the influence of force transmitted from the actuator member through the second force transmitting member to the second cuff as the actuator member moves along the path.

124. A method as set forth in claim 123 wherein said step of moving the actuator member along a path includes moving the actuator member along a path which extends through the joint.

125. A method as set forth in claim 123 wherein said step of moving the actuator member along a path includes effecting relative rotation between internally and externally threaded members to move one of the threaded members connected with the actuator member relative to the other threaded member.

126. A method as set forth in claim 91 wherein said step of connecting a first cuff and a first cuff arm with the first body portion includes engaging an outer side surface of the first body portion with an inner side surface of the first cuff, said method further including gripping the first body portion with the first cuff with sufficient force to prevent relative movement between the outer side surface of the first body portion and the inner side surface of the first cuff during performance of said step of moving the first cuff along the first cuff arm, said step of connecting a second cuff and a second cuff arm with the second body portion includes engaging an outer side surface of the second body portion with an inner side surface of the second cuff, said method further including gripping the second body portion with the second cuff with sufficient force to prevent relative movement between the outer side surface of the second body portion and the inner side surface of the second cuff during performance of said step of moving the second cuff along the second cuff arm.

127. A method as set forth in claim 91 wherein said step of connecting a first cuff and a first cuff arm with the first body portion includes connecting the first cuff arm with the first body portion with a first end portion of the first cuff arm adjacent to the joint, said step of connecting a second cuff and a second cuff arm with the second body portion includes connecting the second cuff arm with the second body portion with a first end portion of the second cuff arm adjacent to the joint and spaced from the first end portion of the first cuff arm and with a base link extending between the first end portions of the first and second cuff arms, said step of bending the joint includes pivoting the first cuff arm about a pivot connection between the base link and the first end portion of the first cuff arm and pivoting the second cuff arm about a pivot connection between the base link and the first end portion of the second cuff arm, the pivot connections between the first and second cuff arms and the base link being spaced apart on the base link.

128. A method as set forth in claim 91 wherein the joint and the first and second body portions define on one side of the joint an inner sector which decreases in angle as the joint is flexed and define on the opposite side of the joint an outer sector which decreases in angle as the joint is extended, said step of bending the joint includes transmitting force from a location in the outer sector to the first and second cuff arms, said step of moving the first cuff along the first cuff arm includes transmitting force from the location in the outer sector to the first cuff, said step of moving the second cuff along the second cuff arm includes transmitting force from the location in the outer sector to the second cuff.

129. A method as set forth in claim 91 wherein the joint and the first and second body portions define on one side of the joint an inner sector which decreases in angle as the joint is flexed and define on the opposite side of the joint an outer sector which decreases in angle as the joint is extended, said step of bending the joint includes pivoting the first cuff arm about a first pivot connection which is disposed in the outer sector and pivoting the second cuff arm about a second pivot connection which is disposed in the outer sector and is spaced from the first pivot connection.

130. A method as set forth in claim 129 wherein said step of connecting the first cuff and the first cuff arm with the first body portion includes connecting the first cuff arm with the first body portion with the first cuff arm disposed in the outer sector, said step of connecting the second cuff and the second cuff arm with the second body portion includes connecting the second cuff arm with the second body portion with the second cuff arm disposed in the outer sector.

131. A method as set forth in claim 91 wherein the joint and first and second body portions define on one side of the joint an inner sector which decreases in angle as the joint is flexed and define on the opposite side of the joint an outer sector which decreases in angle as the joint is extended, said method further including moving an actuator member in the outer sector, said step of bending the joint includes transmitting force from the actuator member through a first link disposed in the outer sector to the first cuff arm and transmitting force from the actuator member through a second link disposed in the outer sector to the second cuff arm during movement of the actuator member.

132. A method as set forth in claim 131 wherein said step of moving the first cuff along the first cuff arm includes transmitting force from the first link to the first cuff during movement of the actuator member, said step of moving the second cuff along the second cuff arm includes transmitting force from the second link to the second cuff during movement of the actuator member.

133. A method of effecting relative movement between first and second body portions which are interconnected by a joint and which define on one side of the joint an inner sector which decreases in angle as the joint is flexed and define on the opposite side of the joint an outer sector which decreases in angle as the joint is extended, said method comprising the steps of connecting a first cuff and a first cuff arm with the first body portion, connecting a second cuff and a second cuff arm with the second body portion, moving an actuator member along a portion of a path disposed in the outer sector, transmitting force from the actuator member to the first cuff arm through a first force transmitting member disposed in the outer sector during movement of the actuator member along the portion of the path disposed in the outer sector, transmitting force from the actuator member to the second cuff arm through a second force transmitting member during movement of the actuator member along the portion of the path disposed in the outer sector and bending the joint under the influence of force transmitted from the actuator member to the first and second cuff arms through the first and second force transmitting members during movement of the actuator member along the portion of the path disposed in the outer sector.

134. A method as set forth in claim 133 further including the steps of moving the first cuff along the first cuff arm under the influence of force transmitted to the first cuff through the first force transmitting member during movement of the actuator member along the portion of the path disposed in the outer sector, and moving the second cuff along the second cuff arm under the influence of force transmitted to the second cuff through the second force transmitting member during movement of the actuator member along the portion of the path disposed in the outer sector.

135. A method as set forth in claim 133 wherein said step of moving the actuator member along the portion of the path disposed in the outer sector includes manually moving an input member disposed in the outer sector and moving the actuator member under the influence of force transmitted to the actuator member from the input member during manual movement of the input member.

136. A method as set forth in claim 135 wherein said step of manually moving the input member is performed by a person having the first and second body portions with which the first and second cuffs are connected.

137. A method as set forth in claim 133 wherein said step of moving the actuator member along the portion of the path disposed in the outer sector includes operating a motor disposed in the outer sector and moving the actuator member under the influence of force transmitted from the motor to the actuator member during operation of the motor.

138. A method as set forth in claim 133 wherein said step of connecting a first cuff and a first cuff arm with the first body portion includes connecting the first cuff arm with the first body portion with a first end portion of the first cuff arm adjacent to the joint, said step of connecting a second cuff and a second cuff arm with the second body portion includes connecting the second cuff with the second body portion with a first end portion of the second cuff arm adjacent to the joint and spaced from the first end portion of the first cuff arm and with a base link extending between the first end portions of the first and second cuff arms, said step of bending the joint includes pivoting the first cuff arm about a pivot connection between the base link and the first end portion of the first cuff arm under the influence of force transmitted to the first cuff arm from the actuator member through the first force transmitting member during movement of the actuator member along the portion of the path disposed in the outer sector and pivoting the second cuff arm about a pivot connection between the base link and the first end portion of the second cuff arm under the influence of force transmitted to the second cuff arm from the actuator member through the second force transmitting member during movement of the actuator member along the portion of the path disposed in the outer sector.

139. A method as set forth in claim 133 wherein said step of moving an actuator member along a portion of a path disposed in the outer sector includes effecting relative rotation between internally and externally threaded members to move one of the threaded members and the actuator member relative to the other threaded member.

140. A method as set forth in claim 133 wherein said step of bending the joint includes bending the joint in extension, said method further including the steps of moving the first cuff along the first cuff arm in a direction toward the joint during bending of the joint and moving the second cuff along the second cuff arm in a direction toward the joint during bending of the joint.

141. A method as set forth in claim 140 wherein said step of bending the joint in extension includes subjecting the joint to a limited amount of distraction.

142. A method as set forth in claim 133 wherein said step of bending the joint includes bending the joint in flexion, said method further including the steps of moving the first cuff along the first cuff arm in a direction away from the joint during bending of the Joint and moving the second cuff along the second cuff arm in a direction away from the joint during bending of the joint.

143. A method as set forth in claim 142 wherein said step of bending the joint in flexion includes subjecting the joint to a limited amount of distraction.

144. A method as set forth in claim 133 further including the step of providing an indication of the degree of flexion of the joint during performance of said step of bending the joint.

145. A method as set forth in claim 133 wherein said step of bending the joint includes pivoting the first cuff arm in a first direction and pivoting the second cuff arm in a second direction which is opposite to the first direction, allowing body tissue to stretch by retaining the first and second cuff arms against pivotal movement after having performed said steps of pivoting the first cuff arm in a first direction and pivoting the second cuff arm in a second direction, and, thereafter, pivoting the first cuff arm in the first direction and pivoting the second cuff arm in the second direction.

146. A method as set forth in claim 133 wherein said step of bending the joint includes bending the joint to one end of the joint's range of motion, holding the joint against movement from the one end of the joint's range of motion for a period of time, and then bending the joint to an end of the joint's range of motion opposite to the one end.

147. A method as set forth in claim 133 wherein said steps of moving an actuator member includes operating a mechanism to move the actuator member in a first direction to bend the joint, said method further including retaining the joint in a condition to which it is bent by resisting movement of the actuator member in a direction opposite to the first direction with resistance provided by the mechanism.

148. A method as set forth in claim 133 wherein said step of moving the actuator member includes moving the actuator member in a first direction from a first position to a second position, interrupting said step of moving the actuator member in a first direction for a period of time upon movement of the actuator member to the second position, and, thereafter, moving the actuator member in the first direction from the second position, said step of bending the joint includes bending the joint in one direction from a first condition to a second condition during movement of the actuator member in the first direction from the first position to the second position, interrupting said step of bending the joint during interruption of said step of moving the actuator member in the first direction, and, thereafter, bending the joint in the one direction from the second condition toward a third condition during movement of the actuator member in the first direction from the second position.

* * * * *

UNITED STATES PATENT AND TRADEMARK OFFICE
CERTIFICATE OF CORRECTION

PATENT NO. : 5,453,075
DATED : September 26, 1995
INVENTOR(S) : Peter M. Bonutti and Gary E. Zitzmann It is certified that error appears in the above-indentified patent and that said Letters Patent is hereby corrected as shown below:

Column 15, line 32, change "2" to --1--.

Column 15, line 33, change "Joint" to --joint--.

Column 27, line 5, change "Wherein" to --wherein--.

Column 27, line 38, change "Wherein" to --wherein--.

Column 28, line 51, change "120" to --121--.

Column 32, line 10, change "Joint" to --joint--.

Signed and Sealed this

Twelfth Day of March, 1996

Attest:

BRUCE LEHMAN

*Attesting Officer*  *Commissioner of Patents and Trademarks*